US009907733B2

(12) United States Patent
Joly et al.

(10) Patent No.: US 9,907,733 B2
(45) Date of Patent: *Mar. 6, 2018

(54) DENTAL COMPOSITIONS COMPRISING ADDITION-FRAGMENTATION AGENTS

(75) Inventors: Guy D. Joly, Shoreview, MN (US); Ahmed S. Abuelyaman, Woodbury, MN (US); Bradley D. Craig, Lake Elmo, MN (US); Afshin Falsafi, Woodbury, MN (US); Joel D. Oxman, Minneapolis, MN (US); Larry R. Krepski, White Bear Lake, MN (US); William H. Moser, Edina, MN (US); Serkan Yurt, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 784 days.

This patent is subject to a terminal disclaimer.

(21) Appl. No.: 14/239,566

(22) PCT Filed: Aug. 14, 2012

(86) PCT No.: PCT/US2012/050718

§ 371 (c)(1),
(2), (4) Date: Jul. 15, 2015

(87) PCT Pub. No.: WO2013/028397

PCT Pub. Date: Feb. 28, 2013

(65) Prior Publication Data

US 2016/0008234 A1    Jan. 14, 2016

Related U.S. Application Data

(60) Provisional application No. 61/526,437, filed on Aug. 23, 2011.

(51) Int. Cl.
*A61K 6/083* (2006.01)
*A61K 6/00* (2006.01)
*A61C 13/15* (2006.01)
*C08L 33/08* (2006.01)

(52) U.S. Cl.
CPC ............ *A61K 6/083* (2013.01); *A61C 19/003* (2013.01); *A61K 6/0023* (2013.01); *A61K 6/0835* (2013.01); *C08L 33/08* (2013.01)

(58) Field of Classification Search
CPC .................................................. A61K 6/083
See application file for complete search history.

(56) References Cited

U.S. PATENT DOCUMENTS

| | | | |
|---|---|---|---|
| 2,801,185 A | 7/1957 | Iler | |
| 4,503,169 A | 3/1985 | Randklev | |
| 4,522,958 A | 6/1985 | Das | |
| 4,547,323 A | 10/1985 | Carlson | |
| 4,886,861 A | 12/1989 | Janowicz | |
| 5,130,347 A | 7/1992 | Mitra | |
| 5,154,762 A | 10/1992 | Mitra | |
| 5,324,879 A | 6/1994 | Hawthorne | |
| 5,501,727 A | 3/1996 | Wang | |
| 5,545,676 A | 8/1996 | Palazzotto | |
| 5,925,715 A | 7/1999 | Mitra | |
| 5,962,550 A | 10/1999 | Akahane | |
| 6,126,922 A | 10/2000 | Rozzi | |
| 6,153,705 A | 11/2000 | Corpart | |
| 6,284,898 B1 | 9/2001 | Moszner | |
| 6,316,519 B1 | 11/2001 | Berge | |
| 6,376,590 B2 | 4/2002 | Kolb | |
| 6,387,981 B1 | 5/2002 | Zhang | |
| 6,572,693 B1 | 6/2003 | Wu | |
| 6,586,483 B2 | 7/2003 | Kolb | |
| 6,670,436 B2 | 12/2003 | Burgath | |
| 6,730,156 B1 | 5/2004 | Windisch | |
| 6,794,520 B1 | 9/2004 | Moszner | |
| 6,900,280 B2 | 5/2005 | Murer | |
| 7,090,721 B2 | 8/2006 | Craig | |
| 7,090,722 B2 | 8/2006 | Budd | |
| 7,156,911 B2 | 1/2007 | Kangas | |
| 7,241,437 B2 | 7/2007 | Davidson | |
| 7,429,422 B2 | 9/2008 | Davidson | |
| 7,649,029 B2 | 1/2010 | Kolb | |
| 7,674,850 B2 | 3/2010 | Karim | |
| 7,888,400 B2 | 2/2011 | Abuelyaman | |
| 7,943,680 B2 | 5/2011 | Bowman | |
| 8,980,969 B2 * | 3/2015 | Joly | C08F 2/38 522/33 |
| 9,410,030 B2 * | 8/2016 | Joly | |
| 9,414,996 B2 * | 8/2016 | Joly | A61K 6/0835 |
| 2005/0175966 A1 | 8/2005 | Falsafi | |
| 2006/0009574 A1 | 1/2006 | Aert | |

(Continued)

FOREIGN PATENT DOCUMENTS

| | | |
|---|---|---|
| EP | 1 217 010 | 8/2004 |
| EP | 2401998 | 1/2012 |

(Continued)

OTHER PUBLICATIONS

Adamson, "Aminoalkyl tertiary carbinols and derived products II 3-Amino-II-di-2-thienyl-alkan-I-ols and -alk-I-enes", Journal of the Chemical Society, 1949, pp. S144-S152.
3M Vitremer Tri-Cure Glass Ionomer System, Dental Products Laboratory, 1992, 36 pages.
Ausiello, "Effect of adhesive layer properties on stress distribution in composite restorations—a 3D finite element analysis", Dental Materials, vol. 18, No. 4, 2002, pp. 295-303.
Benes, "Reactive polymeric carriers obtained by suspension polymerization of hydroxyethyl methacrylate sulphonates", Collect. Czech. Chem. Commun., 1983, vol. 48, No. 11, pp. 3065-3070.
Cara, "Influence of Bis-GMA Derivative Monomer-Based Particulate Composite Resins on the Cuspal Deformation and Microleakage of Restored Teeth", Particulate Science and Technology, 2010, vol. 28; No. 3, pp. 191-206.

(Continued)

*Primary Examiner* — Michael Pepitone
(74) *Attorney, Agent, or Firm* — Kent S. Kokko

(57) ABSTRACT

A curable dental composition comprising an addition-fragmentation agent and a curable dental resin is disclosed.

18 Claims, 1 Drawing Sheet

(56) References Cited

U.S. PATENT DOCUMENTS

| | | |
|---|---|---|
| 2008/0269460 A1 | 10/2008 | Bowman |
| 2009/0011388 A1 | 1/2009 | Craig |
| 2009/0030110 A1 | 1/2009 | Klee |
| 2010/0021869 A1 | 1/2010 | Abuelyaman |
| 2010/0311858 A1 | 12/2010 | Holmes |
| 2011/0196062 A1 | 8/2011 | Craig |
| 2012/0208965 A1 | 8/2012 | Joly |

FOREIGN PATENT DOCUMENTS

| | | |
|---|---|---|
| JP | 2002212210 | 7/2002 |
| WO | WO 1998-01478 | 1/1998 |
| WO | WO 1998-58974 | 12/1998 |
| WO | WO 1999-31144 | 6/1999 |
| WO | WO 1999-35177 | 7/1999 |
| WO | WO 2001-30305 | 5/2001 |
| WO | WO 2001-30307 | 5/2001 |
| WO | WO 2003-063804 | 8/2003 |
| WO | WO 2011-126647 | 10/2011 |
| WO | WO 2012-003136 | 1/2012 |
| WO | WO 2012-112321 | 8/2012 |
| WO | WO 2012-112350 | 8/2012 |
| WO | WO 2013-028401 | 2/2013 |

OTHER PUBLICATIONS

Hutson, "Chain Transfer Activity of ω-Unsaturated Methacrylic Oligomers in Polymerizations of Methacrylic Monomers", Macromolecules, 2004, vol. 37, No. 12, pp. 4441-4452.

Meijs, "Preparation of controlled-molecular-weight, olefin-terminated polymers by free radical methods. Chain transfer using allylic sulfides", Macromolecules, 1988, vol. 21, No. 10, pp. 3122-3124.

Moad, "Chain Transfer Activity of ω-Unsaturated Methyl Methacrylate Oligomers", Macromolecules, 1996, vol. 29, No. 24, pp. 7717-7726.

Moad, "Radical addition—fragmentation chemistry in polymer synthesis", Polymer, 2008, vol. 49, No. 5, pp. 1079-1131.

Oliveira, "Effect of low-elastic modulus liner and base as stress-absorbing layer in composite resin restorations", Dental Materials, 2010, vol. 26, No. 3, pp. e159-e169.

Watts, "Determination of polymerization shrinkage kinetics in visible-light-cured materials: methods development", Dental Materials, Oct. 1991, vol. 7, No. 4, pp. 281-287.

International Search Report for PCT Application No. PCT/US2012/050718 dated Feb. 28, 2013 4 pages.

\* cited by examiner

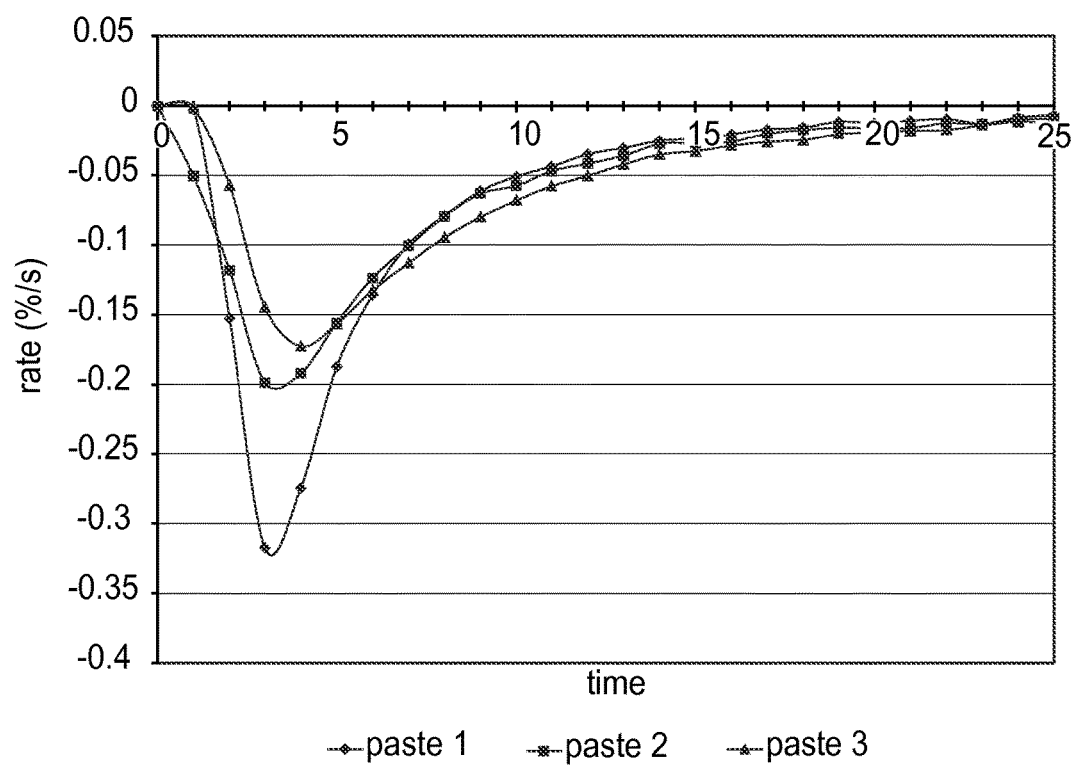

DENTAL COMPOSITIONS COMPRISING ADDITION-FRAGMENTATION AGENTS

CROSS REFERENCE TO RELATED APPLICATION

This application is a national stage filing under 35 U.S.C 371 of PCT/US2012/050718, filed Aug. 14, 2012, which claims priority to Provisional Application No. 61/526,437, filed Aug. 23, 2011, the disclosure of which is incorporated by reference herein in its/their entirety herein.

BACKGROUND

Curable polymeric materials are used in a wide variety of dental applications, including restoratives, cements, adhesives, and the like. Often, such materials shrink upon curing. This is particularly problematic when the material is in a constrained environment, as in a dental filling or restorative, for example. Dimensional changes upon shrinkage while in a constrained environment can generate a strain within the material that is typically converted into a stress on the surrounding environment (e.g., tooth). Such forces can result in interfacial failures between the tooth and the polymeric material resulting in a physical gap and subsequent microleakage into the tooth cavity. Alternatively, such forces can lead to fractures within the tooth and/or the composite.

Generally, conventional processes of curing polymeric dental materials involve a composite held in place on an oral surface with an adhesive and involve curing the adhesive and then subsequently curing the composite material. More specifically, conventional methods utilize one or more of the following steps: surface treatment of the tooth (e.g., etching, priming), application of a curable adhesive to the tooth surface, curing of the adhesive, placement of a composite material (e.g., restorative) on the cured adhesive, and curing of the composite material. There is a need for dental materials, e.g., dental adhesives and dental composites, that reduce the amount of stress placed on the dental material and the surrounding environment during or after curing.

SUMMARY

Although various curable dental compositions have been described, industry would find advantage in compositions having improved properties such as reduced stress deflection and/or reduced shrinkage while maintaining sufficient mechanical properties and depth of cure.

In some embodiments, the present disclosure provides curable dental compositions that are self-adhesive, and require no separate etchant or etching step.

The restoration of dental structures including caries, decayed dentin or decayed enamel, is often accomplished by the sequential application of a dental adhesive and then a dental material (e.g., a restorative material) to the relevant dental structures. Similarly, adhesives are also used in the bonding of dental materials (e.g., orthodontic appliances, generally utilizing an orthodontic adhesive) to a dental structure. Often various pretreatment processes are used to promote the bonding of dental adhesives to dentin or enamel. Typically, such pretreatment steps include etching, for example, using inorganic or organic acids, followed by priming to improve the bonding between the tooth structure and the overlying adhesive.

Whether for application of dental restoratives (e.g., cured or uncured composites such as resin-modified glass ionomers, etc.; fillings; sealants; inlays; onlays; crowns; bridges; etc.) or orthodontic appliances to a dental structure surface, the etchants, primers, and adhesives are typically applied in a step-wise fashion. Often between such steps, one or more rinsing and drying steps are used. As a result, dental restoration and the application of orthodontic appliances typically involve multi-step procedures.

To simplify conventional restorative and/or orthodontic procedures, for example, it would be desirable to provide a single composition that accomplishes both etching and priming. Thus, there is a need for a self-etching primer, particularly a self-etching dental primer, for improved bonding of an adhesive (e.g., a dental adhesive) to a substrate surface (e.g., dental structure, such as dentin, enamel, bone, or other hard tissue) and that could eliminate the conventional post-etching rinsing and drying steps. Furthermore, there is still a need for new compositions that can serve as self-etching adhesives, i.e., dental compositions with priming and etching properties that can be applied in a single pretreatment step. In yet other dental and orthodontic procedures, there is a need for restorative compositions (e.g., filling materials and orthodontic adhesives) that can serve as self-adhesive compositions (preferably i.e., one-part, shelf-stable compositions) that can bond to an untreated dental structure (i.e., a structure not pre-treated with an etchant, primer, or bonding agent). Preferred embodiments of the present disclosure meet these needs.

As used herein, "dental composition" refers to a material, optionally comprising filler, capable of adhering or being bonded to an oral surface. A curable dental composition can be used to bond a dental article to a tooth structure, form a coating (e.g., a sealant or varnish) on a tooth surface, be used as a restorative that is placed directly into the mouth and cured in-situ, or alternatively be used to fabricate a prosthesis outside the mouth that is subsequently adhered within the mouth.

Curable dental compositions include, for example, adhesives (e.g., dental and/or orthodontic adhesives), cements (e.g., resin-modified glass ionomer cements, and/or orthodontic cements), primers (e.g., orthodontic primers), liners (applied to the base of a cavity to reduce tooth sensitivity), coatings such as sealants (e.g., pit and fissure), and varnishes; and resin restoratives (also referred to as direct composites) such as dental fillings, as well as crowns, bridges, and articles for dental implants. Highly filled dental compositions are also used for mill blanks, from which a crown may be milled. A composite is a highly filled paste designed to be suitable for filling substantial defects in tooth structure. Dental cements are somewhat less filled and less viscous materials than composites, and typically act as a bonding agent for additional materials, such as inlays, onlays and the like, or act as the filling material itself if applied and cured in layers. Dental cements are also used for permanently bonding dental restorations such as a crown or bridge to a tooth surface or an implant abutment.

As used herein:

"dental article" refers to an article that can be adhered (e.g., bonded) to a tooth structure or dental implant. Dental articles include, for example, crowns, bridges, veneers, inlays, onlays, fillings, orthodontic appliances and devices.

"orthodontic appliance" refers to any device intended to be bonded to a tooth structure, including, but not limited to, orthodontic brackets, buccal tubes, lingual retainers, orthodontic bands, bite openers, buttons, and cleats. The appliance has a base for receiving adhesive and it can be a flange made of metal, plastic, ceramic, or combinations thereof. Alternatively, the base can be a custom base formed from cured adhesive layer(s) (i.e. single or multi-layer adhesives).

"oral surface" refers to a soft or hard surface in the oral environment. Hard surfaces typically include tooth structure including, for example, natural and artificial tooth surfaces, bone, and the like.

"curable" is descriptive of a material or composition that can be polymerized or crosslinked by a free-radical means such as by irradiating with actinic irradiation to induce polymerization and/or crosslinking; "hardened" refers to a material or composition that has been cured (e.g., polymerized or crosslinked).

"initiator" refers to something that initiates curing of a resin. An initiator may include, for example, a polymerization initiator system, a photoinitiator system, a thermal initiator and/or a redox initiator system.

"self-etching" composition refers to a composition that bonds to a dental structure surface without pretreating the dental structure surface with an etchant. Preferably, a self-etching composition can also function as a self-primer wherein no separate etchant or primer are used.

a "self-adhesive" composition refers to a composition that is capable of bonding to a dental structure surface without pretreating the dental structure surface with a primer or bonding agent. Preferably, a self-adhesive composition is also a self-etching composition wherein no separate etchant is used.

a "dental structure surface" refers to tooth structures (e.g., enamel, dentin, and cementum) and bone.

an "uncut" dental structure surface refers to a dental structure surface that has not been prepared by cutting, grinding, drilling, etc.

an "untreated" dental structure surface refers to a tooth or bone surface that has not been treated with an etchant, primer, or bonding agent prior to application of a self-etching adhesive or a self-adhesive composition of the present invention.

an "unetched" dental structure surface refers to a tooth or bone surface that has not been treated with an etchant prior to application of a self-etching adhesive or a self-adhesive composition of the present invention.

"(meth)acrylate" is a shorthand reference to acrylate, methacrylate, or combinations thereof; "(meth)acrylic" is a shorthand reference to acrylic, methacrylic, or combinations thereof; and "(meth)acryl" is a shorthand reference to acryl, methacryl, or combinations thereof.

"acryloyl" is used in a generic sense and mean not only derivatives of acrylic acid, but also amine, and alcohol derivatives, respectively;

"(meth)acryloyl" includes both acryloyl and methacryloyl groups; i.e. is inclusive of both esters and amides.

"alkyl" includes straight-chained, branched, and cycloalkyl groups and includes both unsubstituted and substituted alkyl groups. Unless otherwise indicated, the alkyl groups typically contain from 1 to 20 carbon atoms. Examples of "alkyl" as used herein include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, and norbornyl, and the like. Unless otherwise noted, alkyl groups may be mono- or polyvalent, i.e monvalent alkyl or polyvalent alkylene.

"heteroalkyl" includes both straight-chained, branched, and cyclic alkyl groups with one or more heteroatoms independently selected from S, O, and N with both unsubstituted and substituted alkyl groups. Unless otherwise indicated, the heteroalkyl groups typically contain from 1 to 20 carbon atoms. "Heteroalkyl" is a subset of "hydrocarbyl containing one or more S, N, O, P, or Si atoms" described below. Examples of "heteroalkyl" as used herein include, but are not limited to, methoxy, ethoxy, propoxy, 3,6-dioxaheptyl, 3-(trimethylsilyl)-propyl, 4-dimethylaminobutyl, and the like. Unless otherwise noted, heteroalkyl groups may be mono- or polyvalent, i.e. monovalent heteroalkyl or polyvalent heteroalkylene.

"aryl" is an aromatic group containing 5-18 ring atoms and can contain optional fused rings, which may be saturated, unsaturated, or aromatic. Examples of an aryl groups include phenyl, naphthyl, biphenyl, phenanthryl, and anthracyl. Heteroaryl is aryl containing 1-3 heteroatoms such as nitrogen, oxygen, or sulfur and can contain fused rings. Some examples of heteroaryl groups are pyridyl, furanyl, pyrrolyl, thienyl, thiazolyl, oxazolyl, imidazolyl, indolyl, benzofuranyl, and benzthiazolyl. Unless otherwise noted, aryl and heteroaryl groups may be mono- or polyvalent, i.e. monovalent aryl or polyvalent arylene.

"(hetero)hydrocarbyl" is inclusive of hydrocarbyl alkyl and aryl groups, and heterohydrocarbyl heteroalkyl and heteroaryl groups, the later comprising one or more catenary oxygen heteroatoms such as ether or amino groups. Heterohydrocarbyl may optionally contain one or more catenary (in-chain) functional groups including ester, amide, urea, urethane, and carbonate functional groups. Unless otherwise indicated, the non-polymeric (hetero)hydrocarbyl groups typically contain from 1 to 60 carbon atoms. Some examples of such heterohydrocarbyls as used herein include, but are not limited to, methoxy, ethoxy, propoxy, 4-diphenylaminobutyl, 2-(2'-phenoxyethoxyl)ethyl, 3,6-dioxaheptyl, 3,6-dioxahexyl-6-phenyl, in addition to those described for "alkyl", "heteroalkyl", "aryl", and "heteroaryl" supra.

BRIEF DESCRIPTION OF THE FIGURES

FIG. 1 is a graph of Watts Shrinkage of curable dental compositions of the Examples.

DETAILED DESCRIPTION

Presently described are dental compositions, dental articles, and methods of use. The dental composition comprises at least one addition-fragmentation agent having the following functional groups: 1) a labile addition-fragmentation group that can cleave and reform to relieve strain, 2) a free-radically polymerizable group which is reactive with the polymerizable component of a dental resin, and 3) a surface-modifying organic functional group that associates with the surface of a substrate, such as a dental structure. The addition-fragmentation agent is labile and free-radically cleavable. In some embodiments, the dental compositions are self-adhesive, i.e., do not require a separate step of etching with an acid to promote bonding of the dental composition to a dental structure. In some embodiments the addition-fragmentation agent may crosslinks a polymer.

The addition-fragmentation agent is of the general formula

where

AF is an addition-fragmentation group;

$R^1$ and $R^3$ are each independently $Z_m$-Q-, $Y_p$-Q'-, a (hetero)alkyl group or a (hetero)aryl group with the proviso that at least one of $R^1$ and $R^3$ is $Z_m$-Q-, and with the proviso that at least one of $R^1$ and $R^3$ is $Y_p$-Q'-, Q is a covalent bond or an organic linking group have a valence of m+1; Q' is a covalent bond or (hetero)hydrocarbyl linking group have a valence of p+1; Z is an ethylenically unsaturated polymerizable group, and Y is a surface-modifying organic functional group that associates with a substrate on which the addition-fragmentation agent is disposed. In some embodiments R' and/or $R^3$ may contain both an ethylenically unsaturated polymerizable group "Z", and a surface-modifying organic functional group "Y".

The addition-fragmentation group "AF" is a labile group that can add, fragment, and add again to the polymer chain to reduce the stress on the growing polymer. Useful addition-fragmentation groups include 1,5-diacyl, 2,2-dimethyl-4-methylene (i.e. derivatives of 2,2-dimethyl-4-methylene-glutaric acid), dithioesters, trithiocarbamates, trithiocarbonates, thiuram disulfides, xanthates vinyl ethers, allyl sulfides, allyl sulfones, allyl sulfoxides, allyl phosphonates, and allyl peroxides.

Suitable addition-fragmentation functionalities or agents for use in the invention also include those functional groups characteristic of conventional reversible addition-fragmentation chain transfer (RAFT) agents. RAFT agents are known to those skilled in the art and are described in G. Moad et al., Radical addition-fragmentation chemistry in polymer synthesis *Polymer*. Vol. 49, No. 5. (3 Mar. 2008), pp. 1079-1131. Examples of RAFT agents are given in U.S. Pat. No. 6,153,705, and published international applications WO 98/01478, WO 99/35177, WO 99/31144 and WO 98/58974. Allylic sulfide chain transfer groups are described by Meijs et al., Macromolecules, 21(10), 3122-3124), 1998. Suitable addition-fragmentation chain transfer agents include trithiocarbonate or allyl sulfide functionalities.

In certain preferred embodiments, the addition fragmentation group is a 1,5-diacyl, 2,2-dimethyl-4-methylene of the formula:

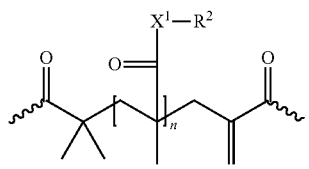

wherein $R^2$ is $Y_m$-Q-, $Y_p$-Q'-, a (hetero)alkyl group or a (hetero)aryl group Q is a covalent bond or a linking group, preferably an organic (hetero)hydrocarbyl linking group having a valence of m+1;

Q' is a covalent bond or an or a linking group, preferably an organic (hetero)hydrocarbyl linking group having a valence of p+1;

Z is an ethylenically unsaturated polymerizable group,

Y is an organic functional group that associates with a substrate on which the addition-fragmentation agent is disposed;

m is 1 to 6;

p is 1 or 2;

n is 0.

The addition-fragmentation agents are preferably derivatives of 2,2-dimethyl-4-methyleneglutaric acid of the following formula:

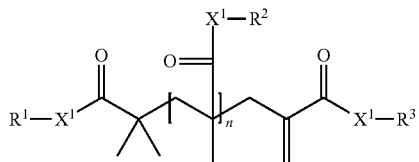

wherein $R^1$, $R^2$ and $R^3$ are each independently $Z_m$-Q-, Y-Q'-, a (hetero)alkyl group or a (hetero)aryl group with the proviso that at least one of $R^1$, $R^2$ and $R^3$ is $Z_m$-Q-, and with the proviso that at least one of $R^1$, $R^2$ and $R^3$ is $Y_p$-Q'—

Q is a covalent bond or a linking group, preferably an organic (hetero)hydrocarbyl linking group having a valence of m+1;

Q' is a covalent bond or an or a linking group, preferably an organic (hetero)hydrocarbyl linking group having a valence of p+1;

Z is an ethylenically unsaturated polymerizable group,

Y is a surface-modifying organic functional group that associates with a substrate on which the addition-fragmentation agent is disposed;

m is 1 to 6;

p is 1 or 2;

$X^1$ is independently —O— or —$NR^4$—, where $R^4$ is H or $C_1$-$C_4$ alkyl, and n is 0 or 1. It will be further understood that each of $R^1$, $R^2$ and $R^3$ may contain both a $Z_m$-Q- and a Y-Q'— group, i.e. both the polymerizable group and the surface-modifying group are part of the same "R" group.

Addition-fragmentation agents according to Formula I are described in U.S. provisional patent application 61/526,470, concurrently filed on Aug. 23, 2011; incorporated herein by reference.

In a favored embodiment, the addition-fragmentation materials ("AFM") of the formula $R^1$-AF-$R^3$, or those of Formula I may be added to a dental composition comprising at least one ethylenically unsaturated monomer or oligomer. Without intending to be bound by theory, it is surmised that the inclusion of such addition-fragmentation material reduces the polymerization-induced stresses, such as by the mechanism described in U.S. provisional patent application 61/526,470, concurrently filed on Aug. 23, 2011, incorporated herein by reference. For embodiments wherein the AFM are multifunctional, comprising at least two ethylenically unsaturated group (e.g. Z is ≥2 in Formula I), the material can function as crosslinking agents, where the crosslinks are labile.

It is believed that the addition-fragmentation agent follows an addition fragmentation pathway as shown in the following Scheme 1. In this scheme the crosslinking agent of Formula I is shown, where n is 0. In the step 1, a free radical species P. adds to the crosslinking agent. The crosslinking agent then fragments as shown in step 2 to form the stable α-carbonyl tertiary radical and the α,β-unsaturated ester bearing the residue of the free radical species P. This α,β-unsaturated ester can undergo radical addition as shown in step 5. The radical addition may be initiated by an initiator or a polymer radical.

Concurrently the α-carbonyl tertiary radical can initiate polymerization of monomer as shown in step 3. For purposes of illustration, a methacrylate monomer is illustrated. On monomer addition, a methacrylate-terminated radical intermediate is produced. In the presence of the crosslinking agent of Formula 1 (as shown in step 4) both addition, and fragmentation, yielding a tertiary radical, occurs.

between the ethylenically unsaturated Z groups will form labile crosslinks. Fragmentation of the addition-fragmentation crosslinking agent provides a mechanism for crosslink

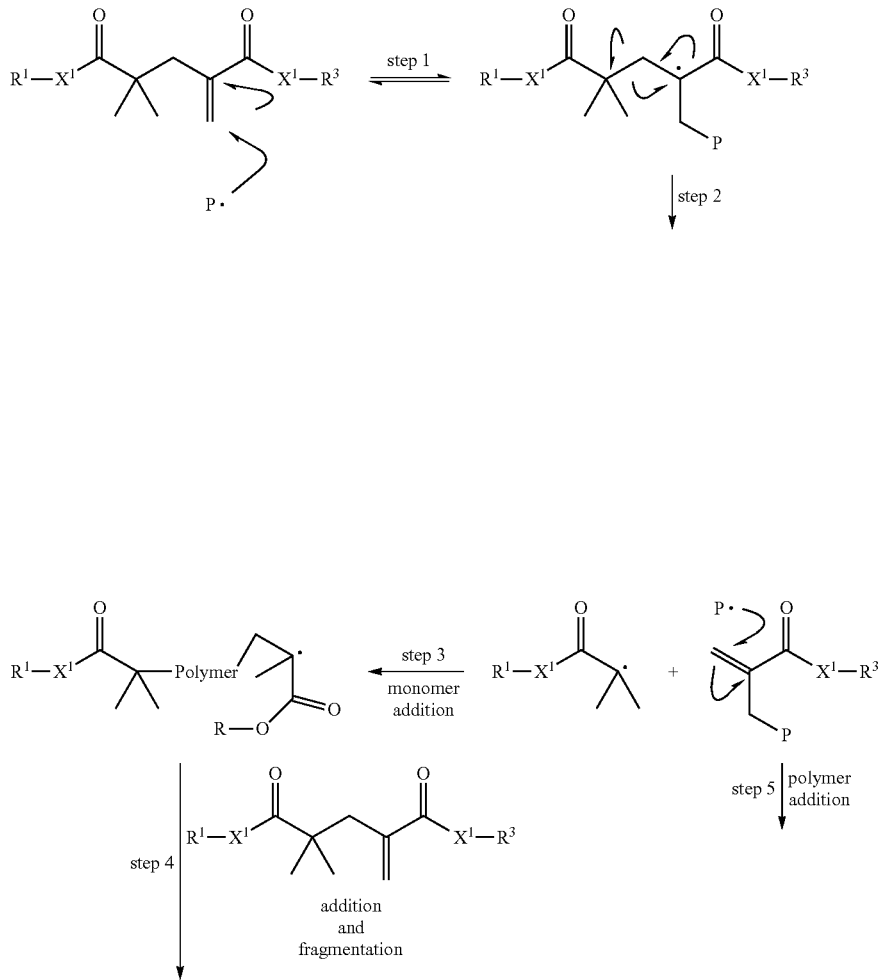

As shown in the following Scheme 2, the addition-fragmentation crosslinking agents provide multiple potential mechanisms for stress relief. A simplified methacrylate polymer is shown crosslinked by the two "Z" groups of the addition fragmentation crosslinking agent. The bonds cleavage. The cleavage of labile crosslinks may allow the polymeric network to relax or reorganize, especially in high stress regions, providing a potential mechanism for stress relief.

Scheme 2
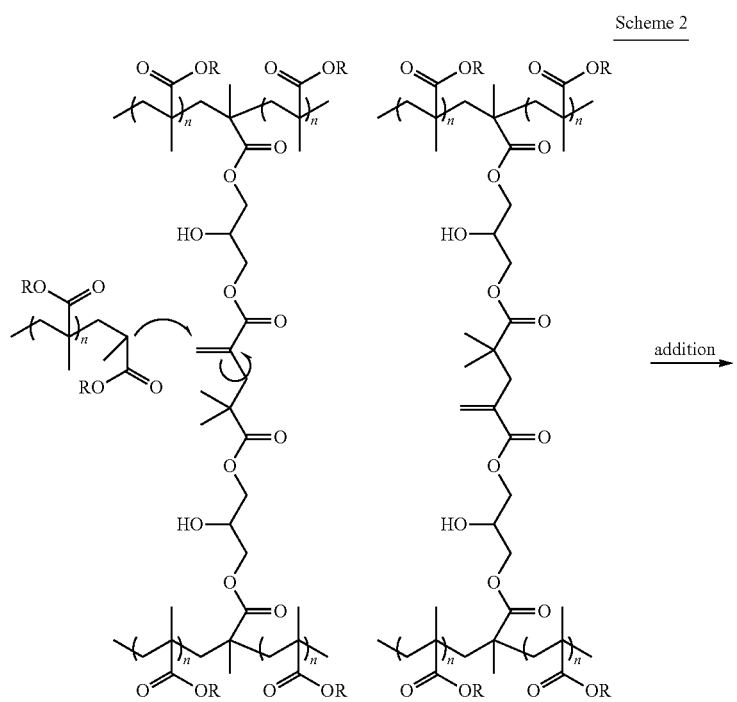
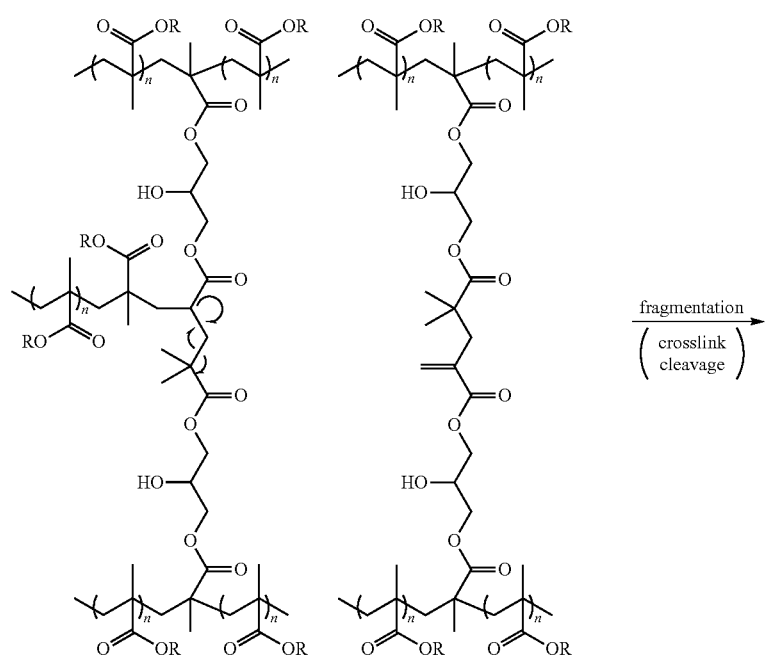

-continued

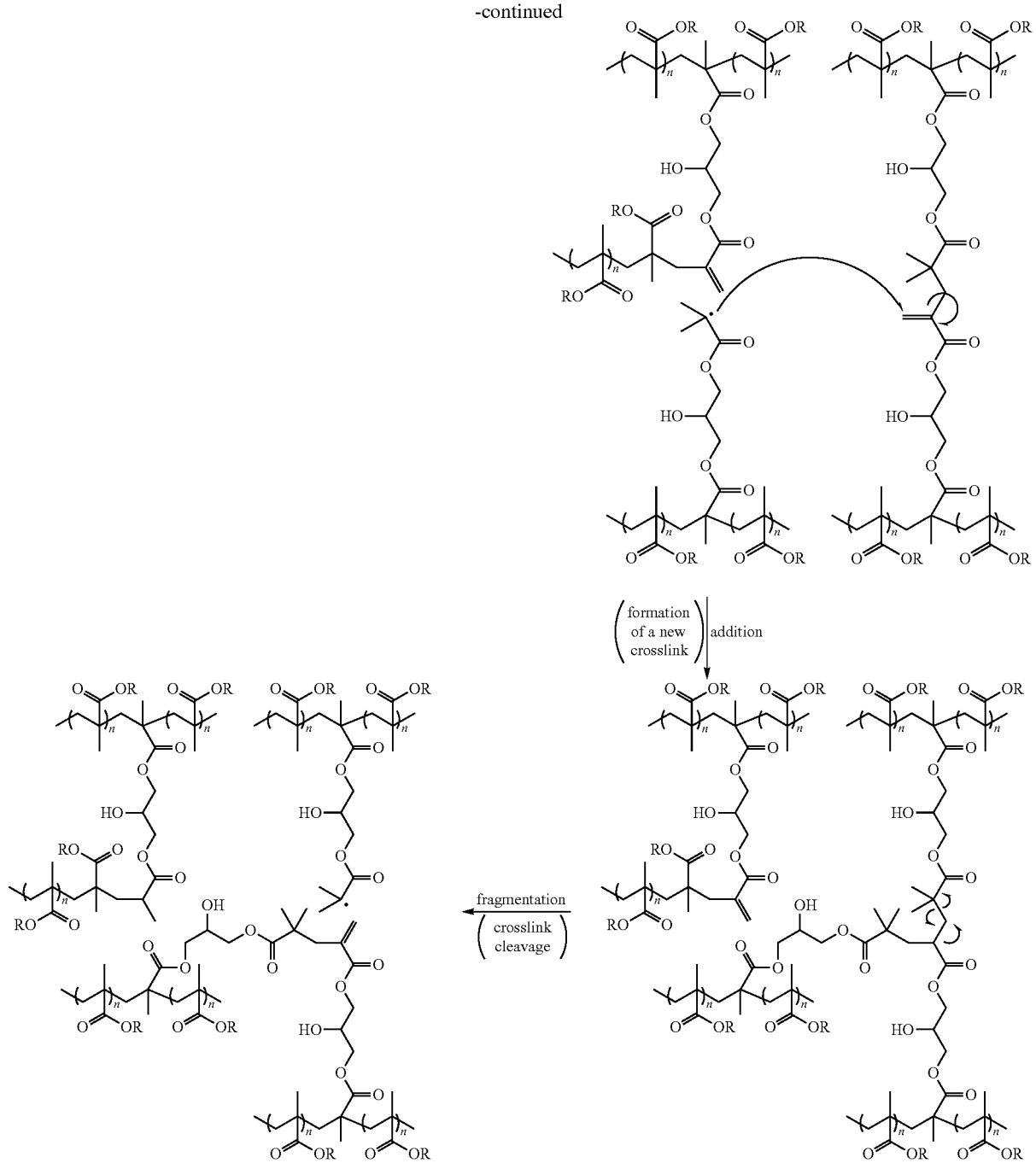

Stress relief could also be a result of attenuated reaction rates (slower cure rates) in the presence of addition-fragmentation materials. The addition of a radical to the addition-fragmentation crosslinking agent generates a potentially long-lived, tertiary radical (the product of step 1, Scheme 1). This long-lived radical intermediate can revert back to starting materials, add to monomer, or fragment. If fragmentation, retro-addition and monomer addition are slow relative to addition, the intermediate tertiary radical will be relatively long-lived. This long-lived radical intermediate will then act as a radical reservoir, slowing down the overall polymerization process. Attenuated cure rates could serve to delay the transition of a material from a viscous material to an elastic solid, delaying the gel point. Post-gel shrinkage is a major component in stress development; therefore, delaying the gel point even slightly may lead to stress relief by allowing additional time for material to flow during the curing process. Therefore, even compounds of Formula I, having a single Z group, may be used to reduce polymerization stress.

The ethylenically unsaturated moiety, Z, of the addition-fragmentation agent may include, but is not limited to the following structures, including (meth)acryloyl, vinyl, styrenic and ethynyl, that are more fully described in reference to the preparation of the compounds below.

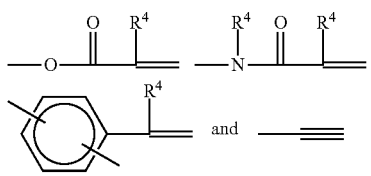

wherein each $R^4$ is independently H or $C_1$-$C_4$ alkyl

In some embodiments, Q is selected from —O—, —S—, —$NR^4$—, —$SO_2$—, —$PO_2$—, —CO—, —OCO—, —$R^6$—, —$NR^4$—CO—$NR^4$—, $NR^4$—CO—O—, $NR^4$—CO—$NR^4$—CO—O—$R^6$—, —CO—$NR^4$—$R^6$—, —$R^6$—CO—O—$R^6$—, —O—$R^6$—, —S—$R^6$—, —$NR^4$—$R^6$—, —$SO_2$—$R^6$—, —$PO_2$—$R^6$—, —CO—$R^6$—, —OCO—$R^6$—, —$NR^4$—CO—$R^6$—, $NR^4$—$R^6$—CO—O—, and $NR^4$—CO—$NR^4$—, wherein each $R^4$ is hydrogen, a $C_1$ to $C_4$ alkyl group, or aryl group, each $R^6$ is a (hetero)hydrocarbyl group including an alkylene group having 1 to 6 carbon atoms, a 5- or 6-membered cycloalkylene group having 5 to 10 carbon atoms, or a divalent arylene group having 6 to 16 carbon atoms, with the proviso that Q-Z does not contain peroxidic linkages.

In some embodiments, Q is an alkylene, such as of the formula —$C_rH_{2r}$—, where r is 1 to 10.

In other embodiments, Q is a hydroxyl-substituted alkylene, such as —$CH_2$—CH(OH)—$CH_2$—. In some embodiments, Q is an aryloxy-substituted alkylene. In some embodiments, $R^5$ is an alkoxy-substituted alkylene.

Z-Q groups are typically selected from $H_2C$=C($CH_3$)C(O)—O—$CH_2$—CH(OH)—$CH_2$—O—, $H_2C$=C($CH_3$)C(O)—O—$CH_2$—CH(O—(O)C($CH_3$)=$CH_2$)—$CH_2$—O—, $H_2C$=C($CH_3$)C(O)—O—CH($CH_2$OAr)—$CH_2$—O—, $H_2C$=C($CH_3$)C(O)—O—$CH_2CH_2$—N(H)—C(O)—O—CH($CH_2$OAr)—$CH_2$—O—., $H_2C$=C($CH_3$)C(O)—O—$CH_2$—CH(O—(O)C—N(H)—$CH_2CH_2$—O—(O)C($CH_3$)C=$CH_2$)—$CH_2$—O—, $H_2C$=C(H)C(O)—O—($CH_2$)$_4$—O—$CH_2$—CH(OH)—$CH_2$—O—, $H_2C$=C($CH_3$)C(O)—O—$CH_2$—CH(O—(O)C—N(H)—$CH_2CH_2$—O—(O)C($CH_3$)C=$CH_2$)—$CH_2$—O—, $CH_3$—($CH_2$)$_7$—CH(O—(O)C—N(H)—$CH_2CH_2$—O—(O)C($CH_3$)C=$CH_2$)—$CH_2$—O—, $H_2C$=C(H)C(O)—O—($CH_2$)$_4$—O—$CH_2$—CH(—O—(O)C(H)=$CH_2$)—$CH_2$—O— and $H_2C$=C(H)C(O)—O—$CH_2$—CH(OH)—$CH_2$—O—. $H_2C$=C(H)C(O)—O—($CH_2$)$_4$—O—$CH_2$—CH(—O—(O)C(H)=$CH_2$)—$CH_2$—O—, and $CH_3$—($CH_2$)$_7$—CH(O—(O)C—N(H)—$CH_2CH_2$—O—(O)C($CH_3$)C=$CH_2$)—$CH_2$—O—, where "Ar" is an aryl group.

With further respect to Formula I, useful Y-Q' groups that may self-adhere or self-etch ($R^1$—$X^1$— groups and optionally $R^2$—X— and $R^3$—$X^1$— groups) include a monophosphate, a phosphonate, a phosphonic acid, a hydroxamic acid, a carboxylic acid, and acetoacetate, an anhydride, an isonitrile group, a silyl, a disulfide, a thiol, an amino, a sulfinic acid, a sulfonic acid, a phosphine, a phenolic (including catechols and 1,2,3-trihydroxy benzene derivatives), or a heterocyclic aromatic group. Of particular interest in dental applications are those Y groups that can bond to, etch, or otherwise associated with a dental structure. Preferred Y groups include a monophosphate, a phosphonate, a phosphonic acid, and a carboxylic acid. The Q' group is selected from —O—, —S—, —$NR^4$—, —$SO_2$—, —$PO_2$—, —CO—, —OCO—, —$R^6$—, —$NR^4$—CO— $NR^4$—, $NR^4$—CO—O—, $NR^4$—CO—$NR^4$— —CO—O—$R^6$—, —CO—$NR^4$—$R^6$—, —$R^6$—CO—O—$R^6$—, —O—$R^6$—. —S—$R^6$—, —$NR^4$—$R^6$—, —$SO_2$—$R^6$—, —$PO_2$—$R^6$—, —CO—$R^6$—, —OCO—$R^6$—, —$NR^4$—CO—$R^6$—, $NR^4$—$R^6$—CO—O—, and $NR^4$—CO—$NR^4$—, wherein each $R^4$ is hydrogen, a $C_1$ to $C_4$ alkyl group, or aryl group, each $R^6$ is a (hetero)hydrocarbyl group, as described for the Q group supra.

In another embodiment, Y is a silyl group of the formula —$SiR^7_3$, wherein each $R^7$ group is independently selected from the group of alkoxy, acetoxy, and halide. Such silyl-functional addition fragmentation agents may bond to silica fillers or other ceramic materials of dental devices and compositions.

The total amount of addition-fragmentation agent(s) in the polymerizable resin portion of the unfilled curable dental composition is typically no greater than 15 wt-%. As the concentration of the addition-fragmentation monomer increases, the stress deflection and Watts Shrinkage typically decrease. However, when the amount of addition-fragmentation agent exceeds an optimal amount, mechanical properties such as Diametral tensile strength and/or Barcol hardness, or depth of cure may be insufficient.

The polymerizable resin portion of the curable dental composition described herein comprises at least 0.1 wt-%, of addition-fragmentation agent(s). Generally, the amount of addition-fragmentation agent is from about 0.5 to 10 wt. % of the polymerizable portion of the unfilled dental composition.

The filled curable dental composition described herein typically comprises at least 0.1 wt-%, of addition-fragmentation agent(s). The total amount of addition-fragmentation agent(s) in the filled curable dental composition is typically no greater than 5 wt-%.

Materials with high polymerization stress upon curing generate strain in the tooth structure. One clinical consequence of such stress can be a decrease in the longevity of the restoration. The stress present in the composite passes through the adhesive interface to the tooth structure generating cuspal deflection and cracks in the surrounding dentin and enamel which can lead to postoperative sensitivity as described in R. R. Cara et al, Particulate Science and Technology 28; 191-206 (2010). Preferred (e.g. filled) dental compositions (useful for restorations such as fillings and crowns) described herein typically exhibit a stress deflection of no greater than 2.0, or 1.8, or 1.6, or 1.4, or 1.2 or 1.0 or 0.8 or 0.6 microns.

The compounds of Formula I may be prepared from (meth)acrylate dimers and trimers by substitution, displacement or condensation reactions. The starting (meth)acrylate dimers and trimers may be prepared by free radical addition of a (meth)acryloyl monomer in the presence of a free radical initiator and a cobalt (II) complex catalyst using the process of U.S. Pat. No. 4,547,323, incorporated herein by reference. Alternatively, the (meth)acryloyl dimers and trimers may be prepared using a cobalt chelate complex using the processes of U.S. Pat. No. 4,886,861 (Janowicz) or U.S. Pat. No. 5,324,879 (Hawthorne), incorporated herein by reference. In either process, the reaction mixture can contain a complex mixture of dimers, trimers, higher oligomers and polymers and the desired dimer or trimer can be separated from the mixture by distillation. Such syntheses are further described in U.S. provisional patent applications 61/442,980 and 61/443,218, filed 15 Feb. 2011 (Incorporated herein by reference) and the forthcoming examples The curable compositions described herein further comprise at least one ethylenically unsaturated resin monomer or oligomer in combination with the addition-fragmentation agent. In some embodiments, such as primers, the ethylenically unsaturated monomer may be monofunctional, having a single (e.g. terminal) ethylenically unsaturated group. In other embodiments, such as dental restorations the ethylenically unsaturated monomer is multifunctional. The phrase "multifunctional ethylenically unsaturated" means that the monomers each comprise at least two ethylenically unsaturated (e.g. free radically) polymerizable groups, such as (meth)acrylate groups.

The amount of curable resin in the dental composition is a function of the desired end use (adhesives, cements, restoratives, etc.) and can be expressed with respect to the (i.e. unfilled) polymerizable resin portion of the dental composition. For favored embodiments, wherein the composition further comprises filler, the concentration of monomer can also be expressed with respect to the total (i.e. filled) composition. When the composition is free of filler, the polymerizable resin portion is the same as the total composition.

In favored embodiments, such ethylenically unsaturated group of the curable dental resin includes (meth)acryloyl such as (meth)acrylamide and (meth)acrylate. Other ethylenically unsaturated polymerizable groups include vinyl and vinyl ethers. The ethylenically unsaturated terminal polymerizable group(s) is preferably a (meth)acrylate group, particularly for compositions that are hardened by exposure to actinic (e.g. UV and visible) radiation. Further, methacrylate functionality is typically preferred over the acrylate functionality in curable dental compositions. The ethylenically unsaturated monomer may comprise various ethylenically unsaturated monomers, as known in the art, for use in dental compositions.

In favored embodiments, the (e.g. dental) composition comprises one or more dental resins having a low volume shrinkage monomer. Preferred (e.g. filled) curable dental compositions (useful for restorations such as fillings and crowns) comprise one or more low volume shrinkage resins such that the composition exhibits a Watts Shrinkage of less than about 2%, preferably no greater than 1.80%, more no greater than 1.60%. In favored embodiments, the Watts Shrinkage is no greater than 1.50%, or no greater than 1.40%, or no greater than 1.30%, and in some embodiments no greater than 1.25%, or no greater than 1.20%, or no greater than 1.15%, or no greater than 1.10%.

Preferred low volume shrinkage monomers include isocyanurate resins, such as described in U.S.S.N. 2011/027523 (Abuelyamen et al.); tricyclodecane resins, such as described in U.S.S.N 2011/041736; polymerizable resins having at least one cyclic allylic sulfide moiety such as described in U.S. Pat. No. 7,888,400 (Abuelyamen et al.); methylene dithiepane silane resins as described in U.S. Pat. No. 6,794,520 (Moszner et al.); and di-, tri, and/or tetra-(meth)acryloyl-containing resins such as described in U.S. 2010/021869 (Abuelyamen et al.); each of which are incorporated herein by reference.

In favored embodiments, the majority of the (e.g. unfilled) polymerizable resin composition comprises one or more low volume shrinkage monomers ("Low shrinkage monomers"). For example, at least 50%, 60%, 70%, 80%, 90% or more of the (e.g. unfilled) polymerizable resin may comprise low volume shrinkage monomer(s).

In one embodiment, the dental composition comprises at least one isocyanurate resin. The isocyanurate resin comprises a trivalent isocyanuric acid ring as an isocyanurate core structure and at least two ethylenically unsaturated (e.g. free radically) polymerizable groups bonded to at least two of the nitrogen atoms of the isocyanurate core structure via a (e.g. divalent) linking group. The linking group is the entire chain of atoms between the nitrogen atom of the isocyanurate core structure and the terminal ethylenically unsaturated group. The ethylenically unsaturated (e.g. free radically) polymerizable groups are generally bonded to the core or backbone unit via a (e.g. divalent) linking group.

The trivalent isocyanurate core structure generally has the formula:

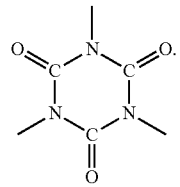

The divalent linking group comprises at least one nitrogen, oxygen or sulfur atom. Such nitrogen, oxygen or sulfur atom forms an urethane, ester, thioester, ether, or thioether linkage. Ether and especially ester linkages can be beneficial over isocyanurate resin comprising urethane linkages for providing improved properties such as reduced shrinkage, and/or increased mechanical properties, e.g., diametral tensile strength (DTS). Thus, in some embodiments, the divalent linking groups of the isocyanurate resin are free of urethane linkages. In some favored embodiments, the divalent linking group comprises an ester linkage such as an aliphatic or aromatic diester linkage.

The isocyanurate monomer typically has the general structure:

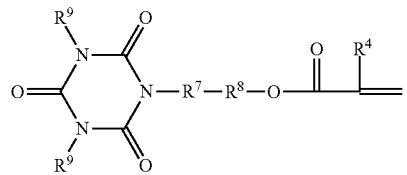

wherein $R^7$ is a (hetero)hydrocarbyl group including straight chain, branched or cyclic alkylene, arylene, or alkarylene, and optionally including a heteroatom (e.g. oxygen, nitrogen, or sulfur); $R^4$ is hydrogen or C1-C4 alkyl; $R^8$ is heterohydrocarbyl group including alkylene, arylene, or alkarylene linking group comprising at least one moiety selected from urethane, ester, thioester, ether, or thioether, and combinations of such moieties; and at least one of the $R^9$ groups is

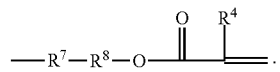

$R^7$ is typically a straight chain, branched or cyclic alkylene, optionally including a heteroatom, having no greater than 12 carbons atoms. In some favored embodiments, $R^7$ has no greater than 8, 6, or 4 carbon atoms. In some favored embodiments, $R_7$ comprises at least one hydroxyl moiety.

In some embodiments, $R^8$ comprises an aliphatic or aromatic ester linkage such as a diester linkage.

In some embodiment, $R^8$ further comprises one or more ether moieties. Hence, the linking group may comprise a combination of ester or diester moieties and one or more ether moieties.

For embodiments, wherein the isocyanurate monomer is a di(meth)acrylate monomer, $R^9$ is hydrogen, alkyl, aryl, or alkaryl, optionally including a heteroatom.

The polymerizable resin portion of the curable unfilled dental composition described herein may comprise at least 10 wt-%, 15 wt-%, 20 wt-%, or 25 wt-%, multifunctional ethylenically unsaturated isocyanurate resin(s). The isocyanurate resin may comprise a single monomer or a blend of two or more isocyanurate resins. The total amount of isocyanurate resin(s) in the unfilled polymerizable resin portion of the curable dental composition is typically no greater than 90 wt-%, 85 wt-%, 80 wt-%, or 75 wt-%.

The filled curable dental composition described herein typically comprises at least 5 wt-%, 6 wt-%, 7 wt-%, 8 wt-%, or 9 wt-% of multifunctional ethylenically unsaturated isocyanurate resin(s). The total amount of isocyanurate resin(s) of the filled hardenable (i.e. polymerizable) dental composition is typically no greater than 20 wt-%, or 19 wt-%, or 18 wt-%, or 17 wt-%, or 16 wt-%, or 15 wt-%.

In another embodiment, the dental composition comprises at least one tricyclodecane resin. The tricyclodecane resin may comprise a single monomer or a blend of two or more tricyclodecane resins. The concentration of multifunctional ethylenically unsaturated tricyclodecane monomer in the (i.e. unfilled) polymerizable resin portion or filled hardenable (i.e. polymerizable) composition can be the same as just described for the multifunctional ethylenically unsaturated isocyanurate monomer.

Tricyclodecane monomers generally have the core structure (i.e. backbone unit (U)):

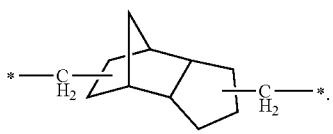

The backbone unit (U) if the tricyclodecane resin typically comprises one or two spacer unit(s) (S) bonded to the backbone unit (U) via an ether linkage. At least one spacer unit (S) comprises a CH(R10)-OG chain, wherein each group G comprises a (meth)acrylate moiety and R10 (comprises at least one group selected from hydrogen, alkyl, aryl, alkaryl and combinations thereof. In some embodiments, R10 is hydrogen, methyl, phenyl, phenoxymethyl, and combinations thereof. G may be bonded to the spacer unit(s) (S) via a urethane moiety.

In some embodiments, the spacer unit(s) (S) typically comprise

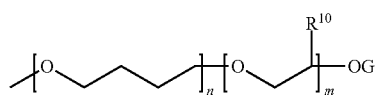

wherein m is 1 to 3; n is 1 to 3; and $R^{10}$ is hydrogen, methyl, phenyl, phenoxymethyl.

In other embodiments, the spacer unit(s) (S) typically comprise

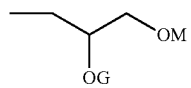

wherein M=aryl.

In some embodiments the composition comprises a multifunctional ethylenically unsaturated isocyanurate monomer and multifunctional ethylenically unsaturated tricyclodecane monomer at a weight ratio ranging from about 1.5:1 to 1:1.5.

In some embodiments, the curable dental composition comprises a polymerizable resin having at least one cyclic allylic sulfide moiety with at least one (meth)acryloyl moiety.

The cyclic allylic sulfide moiety typically comprises at least one 7- or 8-membered ring that has two heteroatoms in the ring, one of which is sulfur. Most typically both of the heteroatoms are sulfur, which may optionally be present as part of an SO, $SO_2$, or S—S moiety. In other embodiments, the ring may comprise a sulfur atom plus a second, different heteroatom in the ring, such as oxygen or nitrogen. In addition, the cyclic allylic moiety may comprise multiple ring structures, i.e. may have two or more cyclic allylic sulfide moieties. The (meth)acryloyl moiety is preferably a (meth)acryloyloxy (i.e. a (meth)acrylate moiety) or a (meth)acryloylamino (i.e., a (meth)acrylamide moiety).

In one embodiment, the low shrinkage resin includes those represented by the formulae:

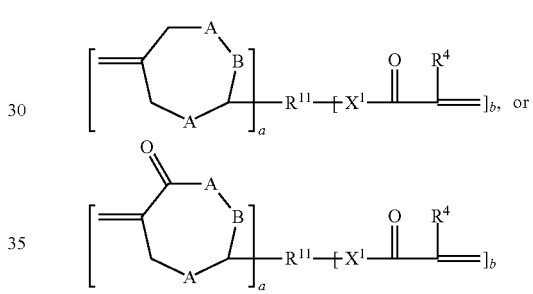

In the above formulae, each A can be independently selected from S, O, N, C (e.g., $C(R^{10})_2$, where each $R^{10}$ is independently a H or an organic group), SO, $SO_2$, N-alkyl, N-acyl, NH, N-aryl, carboxyl or carbonyl group, provided that at least one X is S or a group comprising S. Preferably, each A is sulfur.

B is either alkylene (e.g., methylene, ethylene, etc.) optionally including a heteroatom, carbonyl, or acyl; or is absent, thereby indicating the size of the ring, typically 7- to 10-membered rings, however larger rings are also contemplated. Preferably, the ring is either a 7- or 8-membered ring with Y thus being either absent or methylene, respectively. In some embodiments, Y is either absent or is a C1 to C3 alkylene, optionally including a heteroatom, carbonyl, acyl, or combinations thereof.

$X^1$ is independently —O— or —$NR^4$—, where $R^4$ is H or $C_1$-$C_4$ alkyl.

The $R^{11}$ group represents a linker selected from alkylene (typically having more than one carbon atom, i.e. excluding methylene), alkylene optionally including a heteroatom (e.g., O, N, S, S—S, SO, SO2), arylene, cycloaliphatic, carbonyl, siloxane, amido (—CO—NH—), acyl (—CO—O—), urethane (—O—CO—NH—), and urea (—NH—CO—NH—) groups, and combinations thereof. In certain embodiments, R' comprises an alkylene group, typically a methylene or longer group, that may be either straight chain or branched, and which can be either unsubstituted, or substituted with aryl, cycloalkyl, halogen, nitrile, alkoxy, alkylamino, dialkylamino, akylthio, carbonyl, acyl, acyloxy, amido, urethane group, urea group, a cyclic allylic sulfide moiety, or combinations thereof.

$R^4$ is H or $C_1$-$C_4$ alkyl, and "a" and "b" are independently 1 to 3.

Optionally the cyclic allylic sulfide moiety can further be substituted on the ring with one or more groups selected from straight or branched chain alkyl, aryl, cycloalkyl, halogen, nitrile, alkoxy, alkylamino, dialkylamino, akylthio, carbonyl, acyl, acyloxy, amido, urethane group, and urea group. Preferably the selected substituents do not interfere with the hardening reaction. Preferred are cyclic allylic sulfide structures that comprise unsubstituted methylene members.

A typical low shrinkage monomer can comprise an 8-membered cyclic allylic sulfide moiety with two sulfur atoms in the ring and with the linker attached directly to the 3-position of the ring with an acyl group (i.e., Ring-OC(O)—). Typically the weight average molecular weight (MW) of the hybrid monomer ranges from about 400 to about 900 and in some embodiments is at least 250, more typically at least 500, and most typically at least 800.

The inclusion of a polymerizable compound having at least one cyclic allylic sulfide moiety can result in a synergistic combination of low volume shrinkage in combination with high diametral tensile strength.

In another embodiment, the dental composition comprises a low shrinkage resin that includes at least one di-, tri-, and/or tetra (meth)acryloyl-containing resins having the general formula:

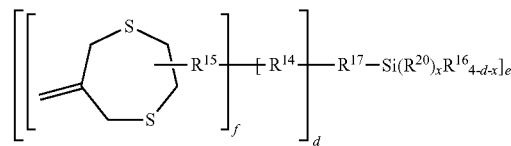

in which $R^{14}$ is a saturated or unsaturated aliphatic or alicyclic hydrocarbon radical with 1 to 10 carbon atoms, which can be interrupted by one or more oxygen and/or sulfur atoms and can contain one or more ester, carbonyl, amide and/or urethane groups, or is an aromatic or heteroaromatic hydrocarbon radical with 6 to 18 carbon atoms, the hydrocarbon radicals being able to be substituted or unsubstituted; $R^{15}$ has one of the meanings given for $R^{14}$ or is absent; $R^{16}$ has one of the meanings given for $R^{14}$ or is absent; $R^{17}$ is equal to —$(CHR^{19})_n$—, —W—CO—NH—$(CHR^{19})_n$—, —Y—CO—NH—$R^{18}$—, —$(CHR^{19})_n$, —$SR^{18}$—, —CO—O—$R^{18}$— or is absent, with n being equal to 1 to 4, $R^{19}$ is hydrogen, $C_1$ to $C_{10}$ alkyl or $C_6$ to $C_{10}$ aryl, $R^{18}$ has one of the meanings given for $R^{14}$ and W stands for an O or S atom or is absent; with $R^{18}$ and $R^{19}$ being able to be substituted or unsubstituted; $R^{20}$ is a hydrolyzable group; d, e, f and x each independently of each other being 1, 2 or 3; and the sum of d+x=2 to 4.

The multifunctional low shrink resins are (e.g. highly) viscous liquids at about 25° C., yet are flowable. The viscosity as can be measured with a Haake RotoVisco RV1

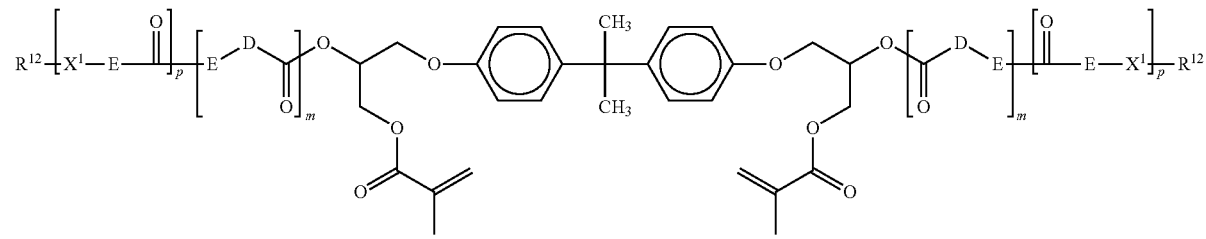

wherein: each $X^1$ is independently —O— or —$NR^4$—, where $R^4$ is H or $C_1$-$C_4$ alkyl;

D and E each independently represent an organic group, and $R^{12}$ represents —$C(O)C(CH_3)$=$CH_2$, and/or (ii) q=0 and $R^2$ represents —H, —$C(O)CH$=$CH_2$, or —$C(O)C(CH_3)$=$CH_2$, with the proviso that at least one $R^{12}$ is a (meth)acrylate; each m is 1 to 5; p and q are independently 0 or 1.

Although, this material is a derivative of bisphenol A, when other low volume shrinkage monomer are employed, such as the isocyanurate and/or tricyclodecane monomer, the dental composition is free of (meth)acrylate monomers derived from bisphenol A.

In another embodiment, the low shrinkage dental resin may be selected from methylene dithiepane silane resins described in U.S. Pat. No. 6,794,520 (Moszner et al.), incorporated herein by reference. Such resins have the general formula device, as described in EP Application No. 10168240.9, filed Jul. 2, 2010 is typically at least 300, or 400, or 500 Pa*s and no greater than 10,000 Pascal-seconds (Pa*s). In some embodiments, the viscosity is no greater than 5000 or 2500 Pa*s.

The ethylenically unsaturated resins of the dental composition are typically stable liquids at about 25° C. meaning that the resins do not substantially polymerize, crystallize, or otherwise solidify when stored at room temperature (about 25° C.) for a typical shelf life of at least 30, 60, or 90 days. The viscosity of the resins typically does not change (e.g. increase) by more than 10% of the initial viscosity.

Particularly for dental restoration compositions, the ethylenically unsaturated resins generally have a refractive index of at least 1.50. In some embodiments, the refractive index is at least 1.51, 1.52, 1.53, or greater. The inclusion of sulfur atoms and/or the present of one or more aromatic moieties can raise the refractive index (relative to the same molecular weight resin lacking such substituents).

In some embodiments, the (unfilled) polymerizable resin may comprise solely one or more low shrink resins in combination with the addition fragmentation agent(s). In other embodiments, the (unfilled) polymerizable resin comprises a small concentration of other monomer(s). By "other" is it meant an ethylenically unsaturated monomer such as a (meth)acrylate monomer that is not a low volume shrinkage monomer.

The concentration of such other monomer(s) is typically no greater than 20 wt-%, 19 wt-%, 18 wt-%, 17 wt-%, 16 wt-%, or 15 wt-% of the (unfilled) polymerizable resin portion. The concentration of such other monomers is typically no greater than 5 wt-%, 4 wt-%, 3 wt-%, or 2 wt-% of the filled polymerizable dental composition.

In some embodiments, the "other monomers" of the dental composition comprises a low viscosity reactive (i.e. polymerizable) diluent. Reactive diluents typically have a viscosity as can be measured with a Haake RotoVisco RV1 device, as described in EP Application No. 10168240.9, filed Jul. 2, 2010 of no greater than 300 Pa*s and preferably no greater than 100 Pa*s, or 50 Pa*s, or 10 Pa*s. In some embodiments, the reactive diluent has a viscosity no greater than 1 or 0.5 Pa*s. Reactive diluents are typically relatively low in molecular weight, having a molecular weight less than 600 g/mole, or 550 g/mol, or 500 g/mole. Reactive diluents typically comprise one or two ethylenically unsaturated groups such as in the case of mono(meth)acrylate or di(meth)acrylate monomers.

In some embodiments, the reactive diluent is an isocyanurate or tricyclodecane monomer. Tricyclodecane reactive diluent may have the same generally structure as previously described. In favored embodiments, the tricyclodecane reactive diluent comprises one or two spacer unit(s) (S) being connected to the backbone unit (U) via an ether linkage; such as described in U.S. 2011/041736 (Eckert et al.); incorporated herein by reference.

Although the inclusion of an addition fragmentation agent in a low volume shrinkage composition typically provides the lowest stress and/or lowest shrinkage, the addition fragmentation agents described herein can also reduce the stress and shrinkage of dental composition comprising conventional hardenable (meth)acrylate monomers, such as ethoxylated bisphenol A dimethacrylate (BisEMA6), 2-hydroxyethyl methacrylate (HEMA), bisphenol A diglycidyl dimethacrylate (bisGMA), urethane dimethacrylate (UDMA), triethlyene glycol dimethacrylate (TEGDMA), glycerol dimethacrylate (GDMA), ethylenegylcol dimethacrylate, neopentylglycol dimethacrylate (NPGDMA), and polyethyleneglycol dimethacrylate (PEGDMA).

The curable component of the curable dental composition can include a wide variety of "other" ethylenically unsaturated compounds (with or without acid functionality), epoxy-functional (meth)acrylate resins, vinyl ethers, and the like.

The (e.g., photopolymerizable) dental compositions may include free radically polymerizable monomers, oligomers, and polymers having one or more ethylenically unsaturated groups. Suitable compounds contain at least one ethylenically unsaturated bond and are capable of undergoing addition polymerization. Examples of useful ethylenically unsaturated compounds include acrylic acid esters, methacrylic acid esters, hydroxy-functional acrylic acid esters, hydroxy-functional methacrylic acid esters, and combinations thereof.

Such free radically polymerizable compounds include mono-, di- or poly-(meth)acrylates (i.e., acrylates and methacrylates) such as, methyl (meth)acrylate, ethyl (meth)acrylate, isopropyl (meth)acrylate, n-hexyl (meth)acrylate, stearyl (meth)acrylate, allyl (meth)acrylate, glycerol tri (meth)acrylate, ethyleneglycol di(meth)acrylate, diethyleneglycol di(meth)acrylate, triethyleneglycol di(meth)acrylate, 1,3-propanediol di(meth)acrylate, trimethylolpropane tri(meth)acrylate, 1,2,4-butanetriol tri(meth)acrylate, 1,4-cyclohexanediol di(meth)acrylate, pentaerythritol tetra(meth)acrylate, sorbitol hex(meth)acrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate tri(meth)acrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500); and vinyl compounds such as styrene, diallyl phthalate, divinyl succinate, divinyl adipate and divinyl phthalate. Other suitable free radically polymerizable compounds include siloxane-functional (meth)acrylates. Mixtures of two or more free radically polymerizable compounds can be used if desired.

The curable dental composition may also contain a monomer having hydroxyl groups and ethylenically unsaturated groups as an example of an "other monomer". Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]propane (bisGMA). Suitable ethylenically unsaturated compounds are available from a wide variety of commercial sources, such as Sigma-Aldrich, St. Louis.

The curable dental compositions can include at least 1 wt-%, at least 3 wt-%, or at least 5 wt-% ethylenically unsaturated compounds with hydroxyl functionality, based on the total weight of the unfilled composition. The compositions can include at most 80 wt-%, at most 70 wt-%, or at most 60 wt-% ethylenically unsaturated compounds with hydroxyl functionality.

The dental compositions described herein may include one or more curable components in the form of ethylenically unsaturated compounds with acid functionality as an example of an "other" monomer. When present, the polymerizable component optionally comprises an ethylenically unsaturated compound with acid functionality. Preferably, the acid functionality includes an oxyacid (i.e., an oxygen-containing acid) of carbon, sulfur, phosphorous, or boron. Such acid-functional "other" monomers contribute to the self-adhesion or self-etching of the dental compositions as described in U.S. 2005/017966 (Falsafi et al.), incorporated herein by reference.

As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, α,β-unsaturated acidic compounds such as glycerol phosphate mono(meth)acrylates, glycerol phosphate di(meth)acrylates, hydroxyethyl (meth)acrylate (e.g., HEMA) phosphates, bis((meth)acryloxyethyl) phosphate, ((meth)acryloxypropyl) phosphate, bis((meth)acryloxypropyl) phosphate, bis((meth)acryloxy)propyloxy phosphate, (meth)acryloxyhexyl phosphate, bis((meth)acryloxyhexyl) phosphate, (meth)acryloxyoctyl phosphate, bis ((meth)acryloxyoctyl) phosphate, (meth)acryloxydecyl phosphate, bis((meth)acryloxydecyl) phosphate, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like, may be used as components. Also monomers, oligomers, and polymers of unsaturated carbonic acids such as (meth)acrylic acids, aromatic (meth)acrylated acids (e.g., methacrylated trimellitic acids), and anhydrides thereof can be used.

The dental compositions can include an ethylenically unsaturated compound with acid functionality having at least one P—OH moiety. Such compositions are self-adhesive and are non-aqueous. For example, such compositions can include: a first compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a $C_1$-$C_4$ hydrocarbon group; a second compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a $C_5$-$C_{12}$ hydrocarbon group; an ethylenically unsaturated compound without acid functionality; an initiator system; and a filler.

The curable dental compositions can include at least 1 wt-%, at least 3 wt-%, or at least 5 wt-% ethylenically unsaturated compounds with acid functionality, based on the total weight of the unfilled composition. The compositions can include at most 80 wt-%, at most 70 wt-%, or at most 60 wt-% ethylenically unsaturated compounds with acid functionality.

The curable dental compositions may include resin-modified glass ionomer cements such as those described in U.S. Pat. No. 5,130,347 (Mitra), U.S. Pat. No. 5,154,762 (Mitra), U.S. Pat. No. 5,925,715 (Mitra et al.) and U.S. Pat. No. 5,962,550 (Akahane). Such compositions can be powder-liquid, paste-liquid or paste-paste systems. Alternatively, copolymer formulations such as those described in U.S. Pat. No. 6,126,922 (Rozzi) are included in the scope of the invention.

An initiator is typically added to the mixture of polymerizable ingredients (i.e. curable resins and AFM). The initiator is sufficiently miscible with the resin system to permit ready dissolution in (and discourage separation from) the polymerizable composition. Typically, the initiator is present in the composition in effective amounts, such as from about 0.1 weight percent to about 5.0 weight percent, based on the total weight of the composition.

The addition-fragmentation agent is generally free-radically cleavable. Although photopolymerization is one mechanism for generating free radicals, other curing mechanisms also generate free radicals. Thus, the addition-fragmentation agent does not require irradiation with actinic radiation (e.g. photocuring) in order to provide the reduction in stress during curing.

In some embodiments, the mixture of resins is photopolymerizable and the composition contains a photoinitiator (i.e., a photoinitiator system) that upon irradiation with actinic radiation initiates the polymerization (or hardening) of the composition. Such photopolymerizable compositions can be free radically polymerizable. The photoinitiator typically has a functional wavelength range from about 250 nm to about 800 nm.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Iodonium salts include diaryl iodonium salts, e.g., diphenyliodonium chloride, diphenyliodonium hexafluorophosphate, and diphenyliodonium tetrafluoroboarate. Some preferred photosensitizers may include monoketones and diketones (e.g. alpha diketones) that absorb some light within a range of about 300 nm to about 800 nm (preferably, about 400 nm to about 500 nm) such as camphorquinone, benzil, furil, 3,3,6,6-tetramethylcyclohexanedione, phenanthraquinone and other cyclic alpha diketones. Of these camphorquinone is typically preferred. Preferred electron donor compounds include substituted amines, e.g., ethyl 4-(N,N-dimethylamino)benzoate.

Other suitable photoinitiators for polymerizing free radically photopolymerizable compositions include the class of phosphine oxides that typically have a functional wavelength range of about 380 nm to about 1200 nm. Preferred phosphine oxide free radical initiators with a functional wavelength range of about 380 nm to about 450 nm are acyl and bisacyl phosphine oxides.

Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Tertiary amine reducing agents may be used in combination with an acylphosphine oxide. Illustrative tertiary amines include ethyl 4-(N,N-dimethylamino)benzoate and N,N-dimethylaminoethyl methacrylate. When present, the amine reducing agent is present in the photopolymerizable composition in an amount from about 0.1 weight percent to about 5.0 weight percent, based on the total weight of the composition. In some embodiments, the curable dental composition may be irradiated with ultraviolet (UV) rays. For this embodiment, suitable photoinitiators include those available under the trade designations IRGACURE and DAROCUR from Ciba Speciality Chemical Corp., Tarrytown, N.Y. and include 1-hydroxy cyclohexyl phenyl ketone (IRGACURE 184), 2,2-dimethoxy-1,2-diphenylethan-1-one (IRGACURE 651), bis(2,4,6-trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl) butanone (IRGACURE 369), 2-methyl-1-[4-(methylthio) phenyl]-2-morpholinopropan-1-one (IRGACURE 907), and 2-hydroxy-2-methyl-1-phenyl propan-1-one (DAROCUR 1173).

The photopolymerizable compositions are typically prepared by admixing the various components of the compositions. For embodiments wherein the photopolymerizable compositions are not cured in the presence of air, the photoinitiator is combined under "safe light" conditions (i.e., conditions that do not cause premature hardening of the composition). Suitable inert solvents may be employed if desired when preparing the mixture. Examples of suitable solvents include acetone and dichloromethane.

Curing is affected by exposing the composition to a radiation source, preferably a visible light source. It is convenient to employ light sources that emit actinic radiation light between 250 nm and 800 nm (particularly blue light of a wavelength of 380-520 nm) such as quartz halogen lamps, tungsten-halogen lamps, mercury arcs, carbon arcs, low-, medium-, and high-pressure mercury lamps, plasma arcs, light emitting diodes, and lasers. In general, useful light sources have intensities in the range of 0.200-1000 W/cm$^2$. A variety of conventional lights for hardening such compositions can be used.

The exposure may be accomplished in several ways. For example, the polymerizable composition may be continuously exposed to radiation throughout the entire hardening process (e.g., about 2 seconds to about 60 seconds). It is also possible to expose the composition to a single dose of radiation, and then remove the radiation source, thereby allowing polymerization to occur. In some cases materials can be subjected to light sources that ramp from low intensity to high intensity. Where dual exposures are employed, the intensity of each dosage may be the same or different. Similarly, the total energy of each exposure may be the same or different.

The dental compositions comprising the multifunctional ethylenically unsaturated monomers may be chemically curable, i.e., the compositions contain a chemical initiator (i.e., initiator system) that can polymerize, cure, or otherwise harden the composition without dependence on irradiation with actinic radiation. Such chemically curable (e.g., polymerizable or curable) composition are sometimes referred to as "self-cure" compositions and may include redox cure systems, thermally curing systems and combinations thereof. Further, the polymerizable composition may comprise a combination of different initiators, at least one of which is suitable for initiating free radical polymerization.

The chemically hardenable compositions may include redox cure systems that include a polymerizable component (e.g., an ethylenically unsaturated polymerizable component) and redox agents that include an oxidizing agent and a reducing agent.

The reducing and oxidizing agents react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical conditions.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. The reducing or oxidizing agents can be microencapsulated as described in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state.

Curable dental compositions can also be cured with a thermally or heat activated free radical initiator. Typical thermal initiators include peroxides such as benzoyl peroxide and azo compounds such as azobisisobutyronitrile, as well as dicumyl peroxide, which is favored for mill blanks.

In favored embodiments, such as when the dental composition is employed as a dental restorative (e.g. dental filling or crown) or an orthodontic cement, the dental composition typically comprises appreciable amounts of (e.g. nanoparticle) filler. The amount of such fillers is a function of the end use—adhesives, cements, restoratives, etc. Such compositions preferably include at least 40 wt-%, more preferably at least 45 wt-%, and most preferably at least 50 wt-% filler, based on the total weight of the composition. In some embodiments the total amount of filler is at most 90 wt-%, preferably at most 80 wt-%, and more preferably at most 75 wt-% filler.

The (e.g. filled) dental composite materials typically exhibit a diametral tensile strength (DTS) of at least about 70, 75, or 80 MPa and/or a Barcol Hardness of at least about 60, or 65, or 70. The depth of cure ranges from about 4 to about 5 and comparable to commercially available (e.g. filled) dental compositions suitable for restorations.

Dental compositions suitable for use as dental adhesives can optionally also include filler in an amount of at least 1 wt-%, 2 wt-%, 3 wt-%, 4 wt-%, or 5 wt-% based on the total weight of the composition. For such embodiments, the total concentration of filler is at most 40 wt-%, preferably at most 20 wt-%, and more preferably at most 15 wt-% filler, based on the total weight of the composition.

Fillers may be selected from one or more of a wide variety of materials suitable for incorporation in compositions used for dental applications, such as fillers currently used in dental restorative compositions, and the like.

The filler can be an inorganic material. It can also be a crosslinked organic material that is insoluble in the polymerizable resin, and is optionally filled with inorganic filler. The filler is generally non-toxic and suitable for use in the mouth. The filler can be radiopaque, radiolucent, or nonradiopaque. Fillers as used in dental applications are typically ceramic in nature.

Non-acid-reactive inorganic filler particles include quartz (i.e., silica), submicron silica, zirconia, submicron zirconia, and non-vitreous microparticles of the type described in U.S. Pat. No. 4,503,169 (Randklev).

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than 12 micrometers, typically no greater than 10 micrometers, and more typically no greater than 5 micrometers as measured using, for example, a sedimentation particle size analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

Other suitable fillers are disclosed in U.S. Pat. No. 6,387,981 (Zhang et al.) and U.S. Pat. No. 6,572,693 (Wu et al.) as well as PCT International Publication Nos. WO 01/30305 (Zhang et al.), U.S. Pat. No. 6,730,156 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. Pat. No. 7,090,721 (Craig et al.), U.S. Pat. No. 7,090,722 (Budd et al.) and U.S. Pat. No. 7,156,911; and U.S. Pat. No. 7,649,029 (Kolb et al.).

Examples of suitable organic filler particles include filled or unfilled pulverized polycarbonates, polyepoxides, poly (meth)acrylates and the like. Commonly employed dental filler particles are quartz, submicron silica, and non-vitreous microparticles of the type described in U.S. Pat. No. 4,503,169 (Randklev).

Mixtures of these fillers can also be used, as well as combination fillers made from organic and inorganic materials.

Fillers may be either particulate or fibrous in nature. Particulate fillers may generally be defined as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs. The macroscopic properties can be highly dependent on the shape of the filler particles, in particular the uniformity of the shape.

Micron-size particles are very effective for improving post-cure wear properties. In contrast, nanoscopic fillers are commonly used as viscosity and thixotropy modifiers. Due to their small size, high surface area, and associated hydrogen bonding, these materials are known to assemble into aggregated networks.

In some embodiments, the dental composition preferably comprise a nanoscopic particulate filler (i.e., a filler that comprises nanoparticles) having an average primary particle size of less than about 0.100 micrometers (i.e., microns), and more preferably less than 0.075 microns. As used herein, the term "primary particle size" refers to the size of a non-associated single particle. The average primary particle size can be determined by cutting a thin sample of hardened dental composition and measuring the particle diameter of about 50-100 particles using a transmission electron micrograph at a magnification of 300,000 and calculating the average. The filler can have a unimodal or polymodal (e.g., bimodal) particle size distribution. The nanoscopic particulate material typically has an average primary particle size of at least about 2 nanometers (nm), and preferably at least about 7 nm. Preferably, the nanoscopic particulate material has an average primary particle size of no greater than about 50 nm, and more preferably no greater than about 20 nm in size. The average surface area of such a filler is preferably at least about 20 square meters per gram ($m^2/g$), more preferably, at least about 50 $m^2/g$, and most preferably, at least about 100 $m^2/g$.

In some preferred embodiments, the dental composition comprises silica nanoparticles. Suitable nano-sized silicas are commercially available from Nalco Chemical Co. (Naperville, Ill.) under the product designation NALCO COLLOIDAL SILICAS. For example, preferred silica particles can be obtained from using NALCO products 1040, 1041, 1042, 1050, 1060, 2327 and 2329.

Silica particles are preferably made from an aqueous colloidal dispersion of silica (i.e., a sol or aquasol). The colloidal silica is typically in the concentration of about 1 to 50 weight percent in the silica sol. Colloidal silica sols that can be used are available commercially having different colloid sizes, see Surface & Colloid Science, Vol. 6, ed. Matijevic, E., Wiley Interscience, 1973. Preferred silica sols for use making the fillers are supplied as a dispersion of amorphous silica in an aqueous medium (such as the Nalco colloidal silicas made by Nalco Chemical Company) and those which are low in sodium concentration and can be acidified by admixture with a suitable acid (e.g. Ludox colloidal silica made by E. I. Dupont de Nemours & Co. or Nalco 2326 from Nalco Chemical Co.).

Preferably, the silica particles in the sol have an average particle diameter of about 5-100 nm, more preferably 10-50 nm, and most preferably 12-40 nm. A particularly preferred silica sol is NALCO™ 1041.

In some embodiments, the dental composition comprises zirconia nanoparticles. Suitable nano-sized zirconia nanoparticles can be prepared using hydrothermal technology as described in U.S. Pat. No. 7,241,437 (Davidson et al.).

In some embodiments, lower refractive index (e.g. silica) nanoparticles are employed in combination with high refractive index (e.g. zirconia) nanoparticles in order to index match (refractive index within 0.02) the filler to the refractive index of the polymerizable resin.

In some embodiments, the nanoparticles are in the form of nanoclusters, i.e. a group of two or more particles associated by relatively weak intermolecular forces that cause the particles to clump together, even when dispersed in a hardenable resin.

Preferred nanoclusters can comprise a substantially amorphous cluster of non-heavy (e.g. silica) particles, and amorphous heavy metal oxide (i.e. having an atomic number greater than 28) particles such as zirconia. The particles of the nanocluster preferably have an average diameter of less than about 100 nm. Suitable nanocluster fillers are described in U.S. Pat. No. 6,730,156 (Windisch et al.); incorporated herein by reference.

In some preferred embodiments, the dental composition comprises nanoparticles and/or nanoclusters surface treated with an organometallic coupling agent to enhance the bond between the filler and the resin. The organometallic coupling agent may be functionalized with reactive curing groups, such as acrylates, methacrylates, vinyl groups and the like and may comprise silane, zirconate or titanate coupling agents. Preferred coupling agents include gamma-methacryloxypropyltrimethoxysilane, gamma-mercaptopropyltriethoxysilane, gamma-aminopropyltrimethoxysilane, and the like.

Suitable copolymerizable organometallic compounds may have the general formulas: $CH_2=C(CH_3)_mSi(OR)_nR_{3-n}$ or $CH_2=C(CH_3)_mC=OOR^{21}Si(OR)_nR_{3-n}$; wherein m is 0 or 1, R is an alkyl group having 1 to 4 carbon atoms, $R^{21}$ is a divalent organic linking group, and n is from 1 to 3.

A variety of conventional methods are available for modifying the surface of nanoparticles including, e.g., adding a surface-modifying agent to nanoparticles (e.g., in the form of a powder or a colloidal dispersion) and allowing the surface-modifying agent to react with the nanoparticles. Other useful surface-modification processes are described in, e.g., U.S. Pat. No. 2,801,185 (Iler), U.S. Pat. No. 4,522,958 (Das et al.) U.S. Pat. No. 6,586,483 (Kolb et al.), each incorporated herein by reference.

Surface-modifying groups may be derived from surface-modifying agents. Schematically, surface-modifying agents can be represented by the formula A-B, where the A group is capable of attaching to the surface of the particle (i.e., the silanol groups of a silica particle) and the B group is a reactive or non-reactive functional group. A non-functional group is one does not react with other components in the system (e.g. the substrate). Non-reactive functional groups can be selected to render the particle relatively more polar, relatively less polar or relatively non-polar. In some embodiments the non-reactive functional group "B" is a hydrophilic group such as an acid group (including carboxylate, sulfonate and phosphonate groups), ammonium group or poly (oxyethylene) group, or hydroxyl group. In other embodiments, "B" may be a reactive functional groups such as an ethylenically unsaturated polymerizable group, including vinyl, allyl, vinyloxy, allyloxy, and (meth)acryloyl, that may be free-radically polymerized with the polymerizable resin or monomers.

Such optional surface-modifying agents may be used in amounts such that 0 to 100%, generally 1 to 90% (if present) of the surface functional groups (Si—OH groups) of the silica nanoparticles are functionalized. The number of functional groups is experimentally determined where quantities of nanoparticles are reacted with an excess of surface modifying agent so that all available reactive sites are functionalized with a surface modifying agent. Lower percentages of functionalization may then be calculated from the result. Generally, the amount of surface modifying agent is used in amount sufficient to provide up to twice the equal weight of surface modifying agent relative to the weight of inorganic nanoparticles. When used, the weight ratio of surface modifying agent to inorganic nanoparticles is preferably 2:1 to 1:10. If surface-modified silica nanoparticles are desired, it is preferred to modify the nanoparticles prior to incorporation into the coating composition.

In some preferred embodiments, the fillers, particularly the silica fillers, may be surface modified with the addition-fragmentation agent of Formula I. Thus the present disclosure provides addition-fragmentation monomer-modified filler particles. These surface modified filler particles may be compounded with the polymerizable mixture and cured as described herein, with the result that the filler particles are integrated into the cured composition. With reference to Formula I, the surface-modified particle filler may be illustrated as:

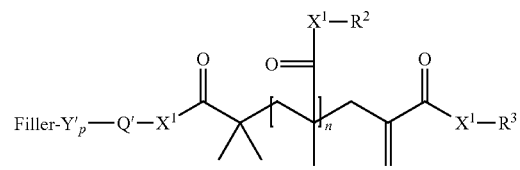

where

Filler is an inorganic filler particle, $R^2$ and $R^3$ are each independently $Z_m$-Q-, $Y_p$-Q'-, a (hetero)alkyl group or a (hetero)aryl group;

Q is a covalent bond or a linking group, preferably an organic (hetero)hydrocarbyl linking group having a valence of m+1;

Q' is a covalent bond or an or a linking group, preferably an organic (hetero)hydrocarbyl linking group having a valence of p+1;

Z is an ethylenically unsaturated polymerizable group,

Y' is the residue of the surface-modifying organic functional group that associates with a substrate on which the addition-fragmentation agent is disposed;

m is 1 to 6;

p is 1 or 2;

$X^1$ is independently —O— or —$NR^4$—, where $R^4$ is H or $C_1$-$C_4$ alkyl, and n is 0 or 1.

It will be understood in the above Formula that the $R^1$ group of formula I was chosen with the "Y-Q'-" surface modifying group and that any of $R^1$, $R^2$ and/or $R^3$ could be illustrated. It will be further understood that each of $R^1$, $R^2$ and $R^3$ may contain both a $Z_m$-Q- and a $Y_p$-Q'- group, i.e. both the polymerizable group and the surface-modifying group are part of the same "R" group.

As used herein the term "residue" is used to define that portion of a functional group remaining reaction of the functional group with the surface of the inorganic particulate For example, the "residue" of a silane functional group Y of the formula —$SiR^7_3$, would be —O—$Si(R^7)_2$—.

For further illustration, the particular filler may be selected from silica (or a silica composite), and the surface-modifying organic functional group "Y" may be selected from a silyl group of the formula —$SiR^7_3$, wherein each $R^7$ group is independently selected from the group of alkoxy, acetoxy, and halide. This would result in a covalent bond between the silica particle and the addition fragmentation agent illustrated by a Silica-O—$Si(R^7)_2$— linkage. It will be understood that the silyl moiety may form one (as illustrated) or more siloxane bonds with a silica particle or siloxane bonds with othyl sily groups. With reference to formula I, one may selected Y=hydroxamic acid or N-hydroxyurea that may bond to zirconia, a filler used in high index coatings/films as well as in dental composites, Y=phosphates and phosphonates would also be useful for alumina fillers, and Y=thiols for gold.

In general, all or a part of the surface functional groups of an inorganic filler particle may be so modified by the addition-fragmentation agent of Formula I. The fillers may be unmodified, surface modified by conventional surface-modifying agents, surface-modifying agent of Formula I, or a mixture of conventional surface-modifying agents and those of Formula I. Preferably, the addition-fragmentation agent is used in amounts of 0.5 to 10 wt. %, relative to the weight of the filler particles.

In some embodiments, a combination of surface modifying agents can be useful, wherein at least one of the agents has a functional group co-polymerizable with a curable resin. Other surface modifying agents which do not generally react with curable resins can be included to enhance dispersibility or rheological properties. Examples of silanes of this type include, for example, aryl polyethers, alkyl, hydroxy alkyl, hydroxy aryl, or amino alkyl functional silanes.

The surface modification can be done either subsequent to mixing with the monomers or after mixing. It is typically preferred to combine the organosilane surface treatment compounds with nanoparticles before incorporation into the resin. The required amount of surface modifier is dependent upon several factors such as particle size, particle type, modifier molecular wt, and modifier type. In general it is preferred that approximately a monolayer of modifier is attached to the surface of the particle.

The surface modified nanoparticles can be substantially fully condensed. Fully condensed nanoparticles (with the exception of silica) typically have a degree of crystallinity (measured as isolated metal oxide particles) greater than 55%, preferably greater than 60%, and more preferably greater than 70%. For example, the degree of crystallinity can range up to about 86% or greater. The degree of crystallinity can be determined by X-ray diffraction techniques. Condensed crystalline (e.g. zirconia) nanoparticles have a high refractive index whereas amorphous nanoparticles typically have a lower refractive index.

In some embodiments, the disclosure provides a universal restorative composite comprising:
a) 15-30 wt % of a curable dental resin comprising at least two polymerizable, ethylenically unsaturated groups;
b) 70-85 wt % of an inorganic filler, preferably a surface modified filler,
c) 0.1 to 10 parts by weight of the addition-fragmentation agent, relative to 100 parts by weight of a) and b), said curable composition further comprising an initiator and <2%, stabilizers, pigments, etc.

In some embodiments, the disclosure provides a flowable restorative (flowable) composite comprising:
a) 25-50 wt % of a curable dental resin comprising at least two polymerizable, ethylenically unsaturated groups;
b) 50-75 wt % of an inorganic filler, preferably a surface modified filler;
c) 0.1 to 10 parts by weight of the addition-fragmentation agent, relative to 100 parts by weight of a) and b), said curable composition further comprising an initiator and <2% initiators, stabilizers, pigments, etc.

In some embodiments, the disclosure provides a resin modified glass-ionomer adhesive comprising:

a) 10-25 wt. % of a partially (meth)acrylated poly(meth)acrylic acid;
b) 5-20% of a hydroxyalkyl (meth)acrylate;
c) 30-60% of fluoroaluminosilicate (FAS) acid reactive glass
d) 0-20% non-acid reactive fillers, preferably surface-treated;
e) 10-20% water; and
f) 0.1 to 10 wt. % of the addition-fragmentation agent, relative to 100 parts by weight of a) and b)),
g) said curable composition further comprising an initiator and <2% stabilizers, pigments, etc.

Preferably the floroaluminosilicate is a silane methacrylate surface-treated floroaluminosilicate.

In some embodiments, the disclosure provides a dental adhesive comprising:
a) 30-8-wt. % mono (meth)acrylate) monomers;
b) 1-10 wt. % polyfunctional (meth)acrylate monomers;
c) 5-60 wt. %% monomers having a acid-functional group (including phosphate, phosphonate, carboxylate, sulfonic acids)
d) 0-10, preferably 1-10 wt. % poly(meth)acrylic acid methacrylate monomers;
e) 0.1 to 10 wt. % of the addition-fragmentation agent, relative to 100 parts by weight of a) to d);
f) an initiator,
g) 0-30% inorganic filler, preferably surface modified, relative to 100 parts by weight of a) to d);
h) 0 to 25 wt. % solvent relative to 100 parts by weight of a) to d);
i) 0 to 25 wt. % water relative to 100 parts by weight of a) to d); and
<2% stabilizers, pigments, etc.

In some embodiments, the dental compositions can have an initial color remarkably different than the cured dental structures. Color can be imparted to the composition through the use of a photobleachable or thermochromic dye. As used herein, "photobleachable" refers to loss of color upon exposure to actinic radiation. The composition can include at least 0.001 wt-% photobleachable or thermochromic dye, and typically at least 0.002 wt-% photobleachable or thermochromic dye, based on the total weight of the composition. The composition typically includes at most 1 wt-% photobleachable or thermochromic dye, and more typically at most 0.1 wt-% photobleachable or thermochromic dye, based on the total weight of the composition. The amount of photobleachable and/or thermochromic dye may vary depending on its extinction coefficient, the ability of the human eye to discern the initial color, and the desired color change. Suitable thermochromic dyes are disclosed, for example, in U.S. Pat. No. 6,670,436 (Burgath et al.).

For embodiments including a photobleachable dye, the color formation and bleaching characteristics of the photobleachable dye varies depending on a variety of factors including, for example, acid strength, dielectric constant, polarity, amount of oxygen, and moisture content in the atmosphere. However, the bleaching properties of the dye can be readily determined by irradiating the composition and evaluating the change in color. The photobleachable dye is generally at least partially soluble in a hardenable resin.

Photobleachable dyes include, for example, Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein, and combinations thereof.

The color change can be initiated by actinic radiation such as provided by a dental curing light which emits visible or near infrared (IR) light for a sufficient amount of time. The mechanism that initiates the color change in the compositions may be separate from or substantially simultaneous with the hardening mechanism that hardens the resin. For example, a composition may harden when polymerization is initiated chemically (e.g., redox initiation) or thermally, and the color change from an initial color to a final color may occur subsequent to the hardening process upon exposure to actinic radiation.

Optionally, compositions may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), and water.

If desired, the compositions can contain additives such as indicators, dyes, pigments, inhibitors, accelerators, viscosity modifiers, wetting agents, buffering agents, radical and cationic stabilizers (for example BHT,), and other similar ingredients that will be apparent to those skilled in the art.

Additionally, medicaments or other therapeutic substances can be optionally added to the dental compositions. Examples include, but are not limited to, fluoride sources, whitening agents, anticaries agents (e.g., xylitol), calcium sources, phosphorus sources, remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents (in addition to the antimicrobial lipid component), antifungal agents, agents for treating xerostomia, desensitizers, and the like, of the type often used in dental compositions. Combinations of any of the above additives may also be employed. The selection and amount of any one such additive can be selected by one of skill in the art to accomplish the desired result without undue experimentation.

The curable dental composition can be used to treat an oral surface such as tooth, as known in the art. In some embodiments, the compositions can be hardened by curing after applying the dental composition. For example, when the curable dental composition is used as a restorative such as a dental filling, the method generally comprises applying the curable composition to an oral surface (e.g. cavity); and curing the composition. In some embodiments, a dental adhesive may be applied prior to application of the curable dental restoration material described herein. Dental adhesives are also typically hardened by curing concurrently with curing the highly filled dental restoration composition. The method of treating an oral surface may comprise providing a dental article and adhering the dental article to an oral (e.g. tooth) surface.

In other embodiments, the compositions can be cured into dental articles prior to applying. For example, a dental article such as a crown may be pre-formed from the curable dental composition described herein. Dental composite (e.g. crowns) articles can be made from the curable composition described herein by casting the curable composition in contact with a mold and curing the composition. Alternatively, dental composite (e.g. crowns) article can be made by first curing the composition forming a mill blank and then mechanically milling the composition into the desired article.

Another method of treating a tooth surface comprises providing a dental composition as described herein wherein the composition is in the form of a (partially cured) curable, self-supporting, malleable structure having a first semi-finished shape; placing the curable dental composition on a tooth surface in the mouth of a subject; customizing the shape of the curable dental composition; and hardening the curable dental composition. The customization can occur in the patient's mouth or on a model outside the patient mouth such as described in U.S. Pat. No. 7,674,850 (Karim et al.); incorporated herein by reference.

Objects and advantages are further illustrated by the following examples, but the particular materials and amounts thereof recited in these examples, as well as other conditions and details, should not be construed to unduly limit this invention. Unless otherwise indicated, all parts and percentages are on a weight basis.

EXAMPLES

All percentages and ratios are by weight unless otherwise specified.

Test Methods

Watts Shrinkage Test Method

The Watts Shrinkage (Watts) Test Method measures shrinkage of a sample test composition by the volumetric change after curing. The sample preparation (90-mg uncured test sample composition) and test procedure were carried out as described in the following reference: Determination of Polymerization Shrinkage Kinetics in Visible-Light-Cured Materials: Methods Development, Dental Materials, October 1991, pages 281-286. The results are reported as negative % shrinkage.

Diametral Tensile Strength (DTS) Test Method

Diametral tensile strength of a cured composition was measured in this test. An uncured test sample composition was injected into a 4-mm (inside diameter) glass tube and the tube was capped with silicone rubber plugs. The tube was compressed axially at approximately 2.88 kg/cm$^2$ pressure for 5 minutes. The sample was then light cured for 80 seconds by exposure to a XL 1500 dental curing light (3M ESPE, St. Paul, Minn.), followed by irradiation for 90 seconds in a Kulzer UniXS curing box (Heraeus Kulzer GmbH, Germany). The test sample was cut with a diamond saw to form disks about 2 mm thick, which were stored in distilled water at 37° C. for about 24 hours prior to testing. Measurements were carried out on an Instron tester (Instron 4505, Instron Corp., Canton, Mass.) with a 10 kilonewton (kN) load cell at a crosshead speed of 1 mm/minute according to ISO Specification 7489 (or American Dental Association (ADA) Specification No. 27). Test results were reported in MPa (megapascals) as the average of multiple measurements.

Stress Test Method

The Stress Test Method measures the stress development during the curing process of a test sample composition. An 8×2.5×2 mm slot was machined in a rectangular 15×8×8 mm aluminum block to form a test fixture for each test sample. The slot was located 2 mm along an edge, thus forming a 2 mm wide aluminum cusp adjacent to and parallel to the 2 mm wide cavity containing compositions to be tested. A linear variable displacement transducer (Model GT 1000, used with an E309 analog amplifier, both from RDP Electronics, United Kingdom) was positioned so as to measure the displacement of the cusp tip as the composition photocured at room temperature. Prior to testing, the slot in the aluminum block was sandblasted using Rocatec Plus Special Surface Coating Blasting Material (3M ESPE, St. Paul, Minn.), treated with RelyX Ceramic Primer (3M ESPE), and finally treated with a dental adhesive, Adper Easy Bond (3M ESPE). The slot was fully packed with approximately 100 mg of the sample compositions. The material was irradiated for 1 minute with a dental curing lamp (Elipar S-10, 3M ESPE) positioned almost in contact (<1 mm) with the material in the slot, then the displacement of the cusp in microns was recorded 9 minutes after the lamp was extinguished.

Depth of Cure Test Method

The depth of cure (DOC) was measured for a test sample composition after curing. A test fixture with an open 8 millimeter stainless steel mold cavity was placed on a polyester film and filled with the sample composition. A second polyester film placed atop the resin and fixture was pressed to provide a level surface on the composition. The filled test fixture was placed on a white background surface and the composition was irradiated for 20 seconds using a dental curing light (3M Dental Products Curing Light 2500 or 3M ESPE Elipar FreeLight2, all made by 3M ESPE Dental Products). After curing, the sample removed was from the mold and the uncured resin was gently removed, e.g., gently scraping materials from the bottom of the sample which was the side that was not irradiated with the curing light. The thickness of the remaining cured material was measured. The reported depths are the actual cured thickness in millimeters divided by 2.

Overlap Shear Test

The overlap shear strength was tested using aluminum test coupons measuring 1×4×1/16 inch (2.54×10.2×0.159 cm). Approximately 2.54 cm of the bonding surface of the coupon was abraded with an abrasive pad (Scotch-Brite Heavy Duty Scour Pad, 3M Company; St. Paul, Minn., USA). The coupon was then cleaned by squirting methyl ethyl ketone (MEK) on the coupon on a paper towel and wiping off the MEK with paper towels. Three coupons were prepared for each test adhesive sample.

An adhesive test sample was prepared by mixing the adhesive composition and dispensing 4 lines of adhesive onto the abraded area such that the adhesive covers a 2.54×1.27 cm area. Spacer beads (3-5 mil (0.0762-0.127 mm) diameter beads (Class VI Soda Lime Glass Sphere beads, MO-SCI Specialty Products; Rolla, Mo., USA) were sprinkled over the adhesive surface. A second coupon was placed over the adhesive such that the adhesive overlap was 2.54 cm×1.27 cm×0.127 mm, and the free ends of the coupons extend in opposite direction. A binder clip was placed over the overlapping portions of the coupons and a second binder clip was placed on the other end of the coupons. The adhesive test sample was allowed to cure 5-7 days at room temperature.

The test was conducted on a tensile testing device with a 5625 lb load cell at a rate of 0.1 inch per minute. The force at failure was recorded in pounds per square inch and reported in megapascals (MPa). Tensile testing devices are available under the trade designations Insight 30 MTS or Sintech 5/GL, from MTS Systems Corporation, Eden Prairie, Minn., USA.

Adhesive Handling Test

The handling of an adhesive composition is evaluated by the wet out of the adhesive on a substrate, and the work life, i.e., how long an adhesive can be worked before gelling and curing. An adhesive test sample was prepared by dispensing 12 dots of (approximately 1.8 cm in diameter) of the adhesive in a row on an 8×2 inch (20.3×5.08 cm) high density polyethylene (HDPE) test coupon. Spacer beads (see Overlap Shear Test) were sprinkled onto the entire adhesive surface of each dot and glass microscope slide coverslips were pressed down over the first 2 dots while a stopwatch was started. After 5 minutes, coverslips were pressed onto the next to dots. This process was continued until all of the dots were covered. The Wet Out Time is reported in minutes as last the time in which the adhesive wets the coverslip sufficiently to create a bond, e.g., if the adhesive wets to the edges of the coverslip at 10 minutes, but not at 15, the Wet Out Time is reported as 10 minutes.

The Work Life of each adhesive was evaluated by gently twisting the coverslip with a wooden applicator stick at one minute intervals starting with the first 2 dots. The Work Life is reported as the time when the coverslip can no longer be moved by the stick.

Adhesive Curing Stress Test

The curing stress that a structural adhesive undergoes during polymerization was evaluated by measuring the deformation of the adhesive on an aluminum shim after curing. A greater curl measurement indicates greater stress in the cured adhesive. The testing procedure and apparatus are described in U.S. patent application Ser. No. 13/169,306, filed Feb. 11, 2012.

Materials—Commercial Reagents were Used as Received from the Vendor 1,2-epoxy-3-phenoxypropane—TCI America, Portland, Oreg., USA 1,2-epoxydecane—from TCI America, Portland, Oreg., USA 2-Isocyantoethyl methacrylate—TCI America, Portland, Oreg., USA 2,6-di-t-butyl-4-methylphenol—Alfa Aesar, Ward Hill, Mass., USA 2-[(methylsulfonyl)oxyethyl]2-methylacrylate—prepared by the procedure reported by M. J. Benes and J. Peska in Collect. Czech. Chem. Commun., 1983, 48, 3065-3070

3-isocyanatopropyltriethoxysilane—Sigma Aldrich, St. Louis, Mo., USA 3-mercaptopropyl)triethoxysilane—Alfa Aesar 3-mercaptopropyl)trimethoxysilane—Alfa Aesar 4-(dimethylamino)pyridine—Alfa Aesar, Ward Hill, Mass., USA 4-hydroxybutyl acrylate glycidylether—Nippon Kasei Chemical, Tokyo, Japan 4-vinylbenzyl chloride—Aldrich, Milwaukee, Wis.

Acryloyl chloride—Sigma Aldrich, St. Louis, Mo., USA

Aerosil 200 silica—Degussa Corporation, Piscataway, N.J., USA

Ammonium hydroxide solution—30% solution—Sigma Aldrich

Benzotriazole—Sigma-Aldrich

BHT—butylated hydroxytoluene, Sigma-Aldrich, Milwaukee, Wis., USA

Bis-EMA-6—Sartomer CD541 (ethoxylated (6 mole ethylene oxide) bisphenol A dimethacrylate, Union Carbide; Piscataway, N.J.

BisGMA—(2,2-Bis[4-(2-hydroxy-3-methacryloyloxy-propoxy)phenyl]propane, Sigma Aldrich Caprolactone—Alfa Aesar, Heysham, Lanc, England Carbon disulfide—EMD Chemicals, Gibbstown, N.J.

CPQ—camphorquinone, Sigma-Alrich

Dibutyltin dilaurate—Alfa Aesar, Ward Hill, Mass., USA

Dichloromethane—EMD Chemicals Inc., Gibbstown, N.J., USA

DPIHFP—Diphenyliodonium hexafluorophosphate (≥98%), Sigma-Aldrich

DMAEMA—2-N,N-dimethylaminoethyl methacrylate, Sigma-Aldrich

DMAP—4-N,N-dimethylaminopyridine, Alfa Aesar, Ward Hill, Mass., USA

DP807 adhesive—2-part curable acrylic resin; 3M Scotch-Weld™ Acrylic Adhesive Resin DP807 Duopak, 3M Company; St. Paul, Minn.

EDMAB—Ethyl 4-N,N-dimethylamino benzoate, Sigma-Aldrich

ENMP—ethyl N-methyl-N-phenyl-3-aminopropionate photoinitiator, CAS No. 2003-76-1; this is the compound of Formula 1-a in U.S. Pat. Appl. No. 2010-0311858 (Holmes) The compound may be synthesized by the methods described by Adamson, et al., JCSOA9; J. Chem. Soc.; 1949; spl.144,152, which is incorporated herein by reference.

Ethanol—Pharmaco-AAPER, Brookfield, Conn., USA

Ethyl acetate—EMD Chemicals Inc., Gibbstown, N.J., USA

GF-31 Silane (3-Methacryloxypropyltrimethoxysilane, Wacker Chemie AG, Munich, Germany)

Glutaric anhydride—Alfa Aesar, Ward Hill, Mass., USA

Glycidyl acrylate—Polysciences Inc., Warrington, Pa., USA

Glycidyl methacrylate—Alfa Aesar, Ward Hill, Mass., USA

HEMA—Hydyroxyethyl methacrylate, Sigma-Aldrich

Irgacure™ 651 photoinitiator obtained from Ciba Specialty Chemicals.

Irgacure™ 819 photoinitiator—BASF Corporation, Ludwigshafen, Germany

Lucirin TPO (2,4,6-Trimethylbenzoyldiphenylphosphine oxide, Polysciences, Inc, Warrington, Pa., USA)

Maleic anhydride—Avocado Research Chemicals, Ltd., Lancashire, England

Methacryloyl chloride—Alfa Aesar, Ward Hill, Mass., USA

Methoxy propanol—J. T. Baker (Mallinkrodt)

Methylene chloride—Sigma Aldrich

MHP—6-methacryloyloxyhexyl phosphate—compound preparation described in U.S. Patent Publication No. 2009-0011388 (Craig, et al.)

Nalco 2329k—41.33 wt % 20 nanometer nanosilica methoxy propanol; Nalco Company; Naperville, Ill.

Nanozirconia filler—silane-treated nanozirconia powder was prepared as described in U.S. Pat. No. 7,156,911, Preparatory Example IA except that SILQUEST A-174 silane was used instead of SILQUEST A-1230. The SILQUEST A-174 was charged at approximately 1.2 millimole silane/g oxide.

Nanosilica filler (also referred to as 20 nm silica)—silane-treated nanosilica powder, with a nominal particle size of 20 nm; prepared as described in U.S. Pat. No. 6,572,693 (column 21, lines 63-67 for nanosized particle filler, Type #2)

Particle A (85 m$^2$/g silica/zirconia nanocluster)—aggregated particle cluster material prepared as described generally in U.S. Pat. No. 6,730,156, Preparatory Example A. The material had a surface area of 85 m$^2$/g, and a weight ratio of silica/zirconia of 73/27. Preparation of the material is more specifically described in U.S. Patent application No. 20110196062, Fillers and Composite Materials with Zirconia and Silica Nanoparticles, (Bradley) paragraphs [0067]-[0073], filed Oct. 9, 2009, and references therein (namely, U.S. Pat. No. 6,376,590 (Kolb, et al.), filed on Oct. 28, 1999, or U.S. Pat. No. 7,429,422 (Davidson et al.), filed Jun. 7, 2007,) each of which is hereby incorporated by reference.

Particle B (125 m$^2$/g silica/zirconia nanocluster)—aggregate powder material prepared in the same manner as Particle A, except that the particles had a surface area of 125 m$^2$/g. The particle ratio is 73/27 by weight silica/zirconia.

PEG 600 DMA—Polyethylene Glycol Dimethacrylate (CAS No. 25852-47-5), Sigma Aldrich Pentaerythritol triacrylate was obtained from Sartomer USA, LLC; Exton, Pa.

Petroleum ether—EMD Chemicals Inc., Gibbstown, N.J., USA

Phosphorus pentoxide ($P_4O_{10}$)—Alfa Aesar, Ward Hill, Mass., USA

Prostab—hydroxy TEMPO, Sigma Aldrich; St. Louis, Mo. USA

Pyridine—Alfa Aesar, Heysham, Lanc, England

SILQUEST A-174 silane—Momentive™ Performance Materials, Albany, N.Y., USA

Sodium hydride—60% dispersion in oil, Alfa Aesar, Ward Hill, Mass.

Succinic anhydride—Alfa Aesar, Ward Hill, Mass., USA

TEGDMA—Triethyleneglycol dimethacrylate, TCI America, Portland, Oreg., USA

Tetrahydrofuran—EMD Chemicals Inc., Gibbstown, N.J., USA

Tin(II)octanoate—Alfa Aesar, Heysham, Lane, England

Toluene—EMD Chemicals Inc., Gibbstown, N.J., USA

Triethyl amine—Sigma Aldrich, St. Louis, Mo., USA

Trimellitic acid anhydride chloride—TCI, Portland, Oreg., USA

Triphenyl antimony—Sigma Aldrich, St. Louis, Mo., USA

Triphenyl phosphine—Alfa Aesar, Ward Hill, Mass., USA

UDMA—Rohamere™ 6661-0 (diurethane dimethacrylate, CAS No. 41 137-60-4), Rohm Tech, Inc., Malden, Mass.

AA/IA/IEM—Polymer made by reacting AA:ITA (acrylic acid:itaconic acid, 4:1 mole ratio) copolymer with sufficient IEM (2-isocyanatoethylmethacrylate) to convert 16 mole percent of the acid groups of the copolymer to pendent methacrylate groups, according to the dry polymer preparation of Example 11 of U.S. Pat. No. 5,130,347.

Z250—Filtek™ Z250 Universal Restorative—3M ESPE Instrumentation—Nuclear magnetic resonance spectra (proton—1H NMR; carbon—13C; phosphorus—31P NMR) were analyzed and recorded using an NMR spectrometer (UltraShield™Plus 400 MHz NMR spectrometer, Bruker Corporation; Billerica, Mass.).

Distillation of Methyl Methacrylate Oligomer Mixture

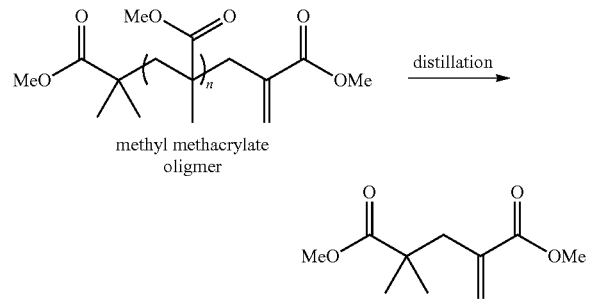

methyl methacrylate oligmer

A methyl methacrylate oligomer mixture was prepared according to the procedure described in Example 1 of U.S. Pat. No. 4,547,323 (Carlson, G. M.). The mixture was distilled as described in Moad, C. L.; Moad, G.; Rizzardo, E.; and Thang, S. H. *Macromolecules*, 1996, 29, 7717-7726, with details as follows:

A 1 liter round-bottomed flask equipped with a magnetic stir bar was charged with 500 g of the methyl methacrylate oligomer mixture. The flask was fitted with a Vigreux column, a condenser, a distribution adapter, and four collection flasks. The distillation apparatus was placed under reduced pressure (0.25 mm Hg) at room temperature and stirred continuously until gas evolution (indicating removal of methyl methacrylate monomer) had largely subsided. The flask was then heated to reflux in an oil bath to distill the oligomer mixture. The fractions isolated by this procedure are listed in Table 1

TABLE 1

Fractions from the Distillation of Methyl Methacrylate Oligomer Mixture

| Fraction | Pressure (mm Hg) | Boiling point (° C.) | Mass (g) | Approximate Composition |
|---|---|---|---|---|
| A | 0.25 | 59 | 63.27 | Dimer |
| B | 0.09 | 47 | 115.97 | Dimer |
| C | 0.10 | 60-87 | 25.40 | dimer (~50-75%), oligomers (mainly trimer) |
| D | 0.10 | 87 | 15.20 | dimer (~5%), oligomers (mainly trimer) |
| E | 0.13 | 105 | 156.66 | oligomers (trimer and higher) |

Hydrolysis of Methyl Methacrylate Dimer

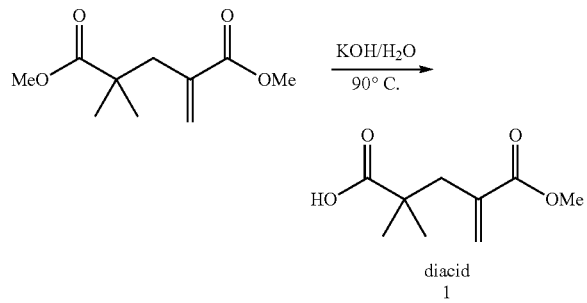

The dimer from Fraction B was hydrolyzed to diacid 1 as described in Hutson, L.; Krstina, J.; Moad, G.; Morrow, G. R.; Postma, A.; Rizzardo, E.; and Thang, S. H. *Macromolecules*, 2004, 37, 4441-4452, with details as follows:

A 1 liter, round-bottomed flask equipped with a magnetic stir bar was charged with deionized water (240 ml) and potassium hydroxide (60.0 g, 1007 millimole). The mixture was stirred until homogeneous. Methyl methacrylate dimer (75.0 g, 374.6 millimole) from Fraction B) was added. The flask, equipped with a reflux condenser, was heated to 90° C. in an oil bath. After 17 hours, the flask was removed from the oil bath and allowed to cool to room temperature. The reaction solution was acidified to pH of approximately 1 by adding concentrated HCl. A white precipitate formed upon acidification. The heterogeneous mixture was vacuum filtered and quickly washed twice with 50-100 ml of deionized water. The white solid was dried by pulling air through the solid for approximately 4 hours. The white solid was then dissolved in approximately 1750 ml of dichloromethane. Less than 1 gram of solid remained insoluble. The solution was allowed to stand for 24 hours and then vacuum filtered to remove the undissolved white solid. The filtered dichloromethane solution was concentrated in vacuum to provide a white solid. The solid was further dried under high vacuum to provide diacid 1 (55.95 g, 325.0 millimole, 87%) as a white powder.

Preparation of AFM-1

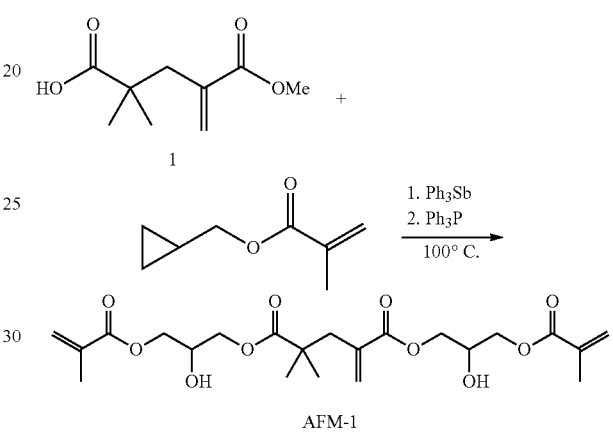

An approximately 250 ml amber bottle equipped with a magnetic stir bar was charged with glycidyl methacrylate (23.0 ml, 24.8 g, 174 millimole) and triphenyl antimony (0.369 g, 1.04 millimole). The bottle was covered with a plastic cap with two 16 gauge needles pierced through the cap and remained in the cap which to allowed air into the reaction. The mixture was heated to 100° C. in an oil bath while stirring. Diacid 1 (15.0 g, 87.1 millimole) was added to the reaction in small portions over a period of 1.5 hours. After 21 hours, triphenyl phosphine (0.091 g, 0.35 millimole) was added. The reaction was stirred at 100° C. for an additional 6.5 hours. A sample from the reaction mixture at this point was analyzed and 1H NMR analysis confirmed the structure of AFM-1 as a mixture of isomers, and also indicated consumption of glycidyl methacrylate. The reaction was cooled to room temperature to provide AFM-1 as a clear, very pale yellow viscous material.

Example 1

Preparation of AFM-Glutarate

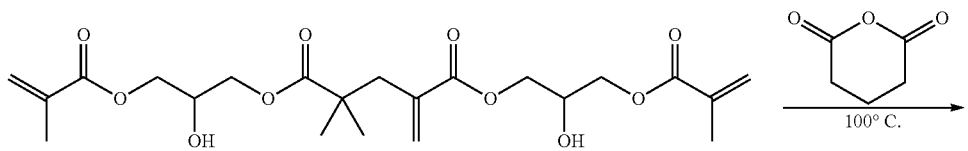

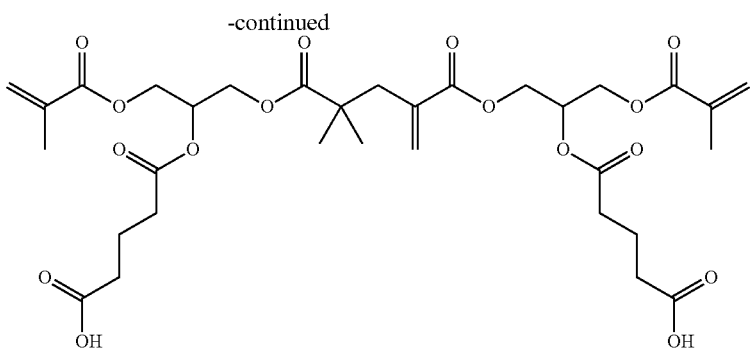

AFM-glutarate

An approximately 25 ml amber bottle equipped with a magnetic stir bar was charged with AFM-1 (5.00 g, 10.95 millimole) and glutaric anhydride (2.50 g, 21.91 millimole). The bottle was covered with a piece of aluminum foil with three small holes to vent the reaction to air. The reaction was heated to 100° C. with stirring. After 25.25 hours, the reaction was cooled to room temperature and sampled. A small amount of glutaric acid remained according to $^1$H NMR analysis. The reaction was heated back 100° C. with stirring. After an additional 24 hours, the reaction was cooled to room temperature. $^1$H NMR analysis confirmed the structure AFM-glutarate as a mixture of isomers. AFM-glutarate (7.39 g, 10.8 millimole, 99%) was obtained as a very viscous, very pale yellow oil.

Example 2

Preparation of AFM-Phosphate

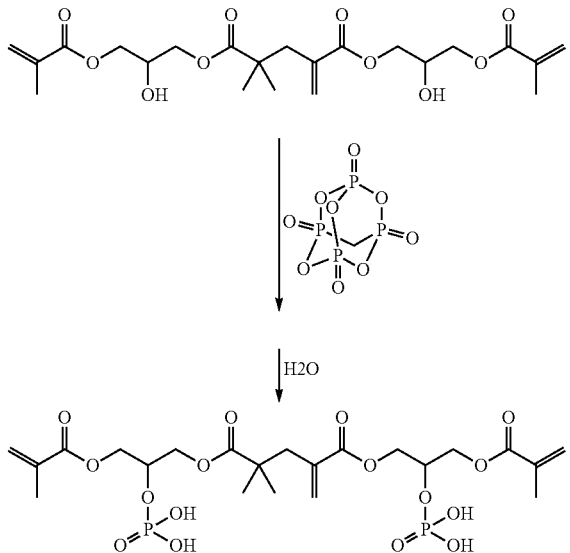

Phosphorus pentoxide (2.06 g, 0.00725 mole) was suspended in dichloromethane in a glass jar equipped with a magnetic stirring bar. AFM-1 (6.6 g, 0.0144 mol) was added and the mixture was stirred at room temperature for 4 hours. Water (0.25 g, 0.014 mole) was then added and the mixture became clear, leaving a small amount of insoluble residue separated at the bottom of the jar. Stirring was continued for 3 hours, and then the mixture was left at room temperature undisturbed overnight. The clear part of the mixture on top was decanted into a round bottom flask followed by solvent removal in a rotary evaporator to provide a clear pale yellow viscous liquid. Yield of the reaction was 85%. The structure of product was confirmed by 1H and 31P NMR.

Example 3

Preparation of AFM-Succinate

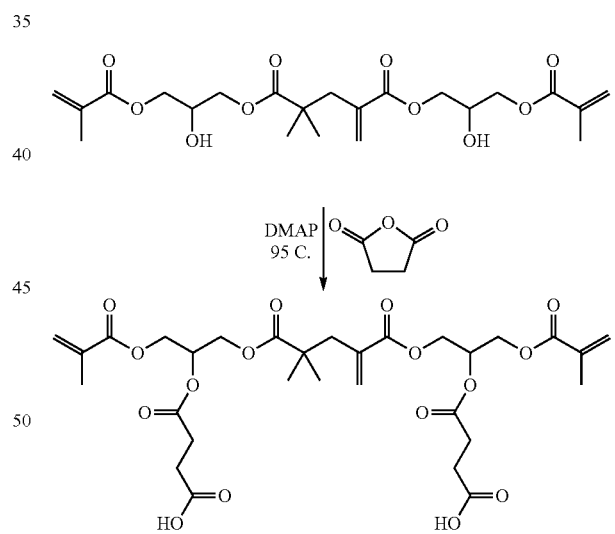

AFM-1 (5.95 g, 0.013 mol), succinic anhydride (2.55 g, o.255 mol) DMAP (80 mg) BHT (8 mg) were charged into a 50 mL round-bottom flask equipped with a magnetic stirring bar and a dry air blanket. The flask was heated in an oil bath at 95-100° C. with continuous stirring for 5 hours. The heat was turned off and the product was collected with essentially 100% yield as a clear light yellow liquid. The structure of AFM-succinate was confirmed by 1H and 13C NMR.

Example 4

Preparation of AFM-Maleate

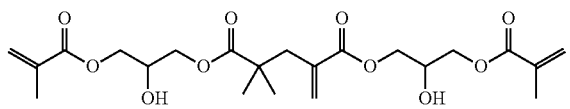

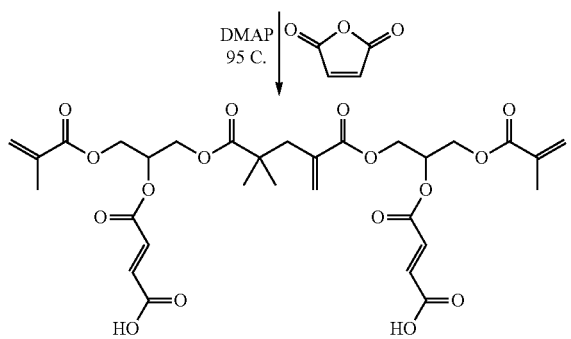

AFM-maleate was prepared from AFM-1 (6.6 g, 0.0145 mol) and maleic anhydride (Avocado Research Chemicals, Ltd, Lancashire, England) (2.8 g, 0.028 mol) in a similar procedure used for the preparing the AFM-succinate. The yield of the reaction was essentially 100%. AFM-maleate was isolated as a clear red-colored liquid and the structure was confirmed by 1H and 13C NMR.

Examples 5-7

Control Example C1—Compositions with AFM Materials

Compositions were prepared by mixing the materials shown in Table 2 using the acidic AFMs of Examples 2-4 as shown. The values are in percent by weight. A Control composition C1 was prepared with MHP in place of the AFM materials.

The compositions were tested for curing and stress relief by painting each resin onto a strip of paper, blow drying with an air gun and then curing for 80 seconds using a 3M Curing Light XL3000 (3M Company; St. Paul, Minn.).

All of the compositions cured to a solid film indicating sufficient cure. Examples 5-7 remained flat after curing while the Control curled. The flatness was attributed to the addition of the acidic AFMs as stress relievers.

TABLE 2

| Component | Compositions in Percent By Weight | | | |
|---|---|---|---|---|
| | Ex C1 | Ex 5 | Ex 6 | Ex 7 |
| BHT | 0.1 | 0.1 | 0.1 | 0.1 |
| EDMAB | 0.97 | 0.97 | 0.97 | 0.97 |
| CPQ | 1.55 | 1.55 | 1.55 | 1.55 |
| Lucirin TPO | 2.31 | 2.31 | 2.31 | 2.31 |
| AA/IA/IEM | 3.18 | 3.18 | 3.18 | 3.18 |
| HEMA | 22.26 | 22.26 | 22.26 | 22.26 |
| BisGMA | 18.6 | 18.6 | 18.6 | 18.6 |
| DMAEMA | 2.44 | 2.44 | 2.44 | 2.44 |
| MHP | 15.15 | | | |
| AFM-phosphate | | 15.15 | | |
| AFM-succinate | | | 15.15 | |
| AFM-maleate | | | | 15.15 |
| Water | 10.62 | 10.62 | 10.62 | 10.62 |
| Ethanol | 12.55 | 12.55 | 12.55 | 12.55 |
| Aerosil 200 | 7.72 | 7.72 | 7.72 | 7.72 |
| Silane GF31 | 2.55 | 2.55 | 2.55 | 2.55 |

Example 8

Preparation of AFM-Silane

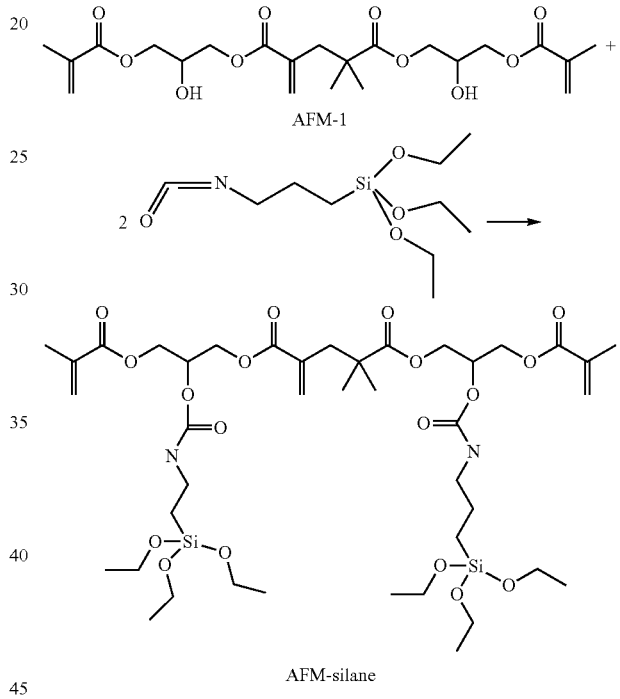

AFM-silane

An AFM-silane was prepared by mixing AFM-1 (3.00 g), 3-isocyanatopropyltriethoxysilane (3.24 g), and 1 drop of dibutyltin dilaurate in a container. The mixture was allowed to react overnight at room temperature (approximately 23° C.). The AFM-Silane was confirmed by analysis through Fourier Transform Infrared spectroscopy (FTIR,) showing the loss of isocyanate peak from the silane.

Example 9

Filler 1

A filler was prepared by mixing 50.03 g of Particle B, 4.51 g of GF-31 silane 0.77 g of AFM-Silane, 58 g of ethyl acetate, and catalyzing the reaction with 1.004 g of 30% ammonium hydroxide solution. The mixture was stirred overnight on a stir plate at room temperature. The solvent was flashed off in a fume hood the next morning, and heated for 30 min at 85° C. to complete the reaction. The particles contained 1.5% AFM-silane.

Example 10

Filler 2

A filler was prepared as in Example 9 except that 50.00 g of Particle B, 1.27 g of AFM-silane, 4.01 g of GF-31 Silane, 1.055 g of 30% ammonium hydroxide solution, and 50.7 g of ethyl acetate were used. The particles contained 2.5% AFM-silane.

Example 11

Filler 3

A filler was prepared as in Example 9 except 50.07 g of Particle B, 2.51 g of AFM-Silane, 2.753 g of GF-31, 1.041 g of 30% ammonium hydroxide solution, and 50.6 g ethyl acetate were used. The particles contained 5% AFM-Silane.

Example 12

Filler 4

A filler was prepared as in Example 9 except that 29.98 g of Particle A 0.965 g of AFM-silane, 1.61 g of GF-31 silane, 41.7 g ethyl acetate and 0.64 g 30% ammonium hydroxide solution were used.

Examples 13-14

Control Example C2—Paste Compositions

A dental resin composition was prepared by stirring the components shown in Table 3 at approximately 45° C. until all components were dissolved.

TABLE 3

| Dental Resin Composition | |
| --- | --- |
| Component | Amount in weight % |
| BisGMA | 13.94 |
| 90/10 Resin (BisGMA/TEGDMA) | 11.82 |
| UDMA Resin | 34.40 |
| BisEMA6 Resin | 34.40 |
| PEG 600 DMA | 3.74 |
| CPQ | 0.22 |

TABLE 3-continued

| Dental Resin Composition | |
| --- | --- |
| Component | Amount in weight % |
| DPIHFP | 0.35 |
| IRGACURE 819 | 0.05 |
| ENMP | 0.81 |
| BHT | 0.15 |
| Benzotriazole | 0.12 |

Example C2 (Paste1) was a paste prepared by mixing 4.40 g of the dental resin with 0.82 g of Nanozirconia filler 1.5216 g of Nanosilica filler, and 13.26 g of Particle B to form a uniform mixture.

Example 13 (Paste 2) was a paste prepared by mixing 13.26 g of the filler from Example 10 (Filler 2), 0.83 g of Nanozirconia filler, 1.54 g of Nanosilica filler and 4.4021 g of dental resin to form a uniform mixture.

Example 14 (Paste 3) was a paste prepared by mixing 4.40 g of dental resin, 0.83 g of Nanozirconia filler, 1.52 g of Nanosilica filler and 13.26 g of the filler of Example 11 (Filler 3) to form a uniform mixture.

The pastes for each example were tested according to the above described test methods for the rate of shrinkage in the Watts Shrinkage Test Method, and for mechanical properties in the Diametral Tensile Strength Test Method.

The rate of shrinkage (determined from the slope of the raw shrinkage data) is shown in FIG. 1. As can be seen from the data, a significant reduction in the shrinkage rate (which has been found to correspond to stress measurements), was seen with increasing levels of the AFM-Silane material. Paste 1 contained only GF-31 (3-methacryloxypropyltrimethoxysilane), whereas Pastes 2 and 3 had increasing amounts of the AFM-Silane on the cluster filler that was incorporated into the formulation.

The diametral tensile strength test results in Table 4 show that the AFM-Silane treated particles provide acceptable mechanical properties for dental composites.

TABLE 4

| Diametral Tensile Strength | |
| --- | --- |
| Example | Diametral Tensile Strength (MPa) |
| 13 | 80.7 |
| 14 | 76.3 |
| C2 | 70.9 |

Example 15

Preparation of AFM-Caprolactone

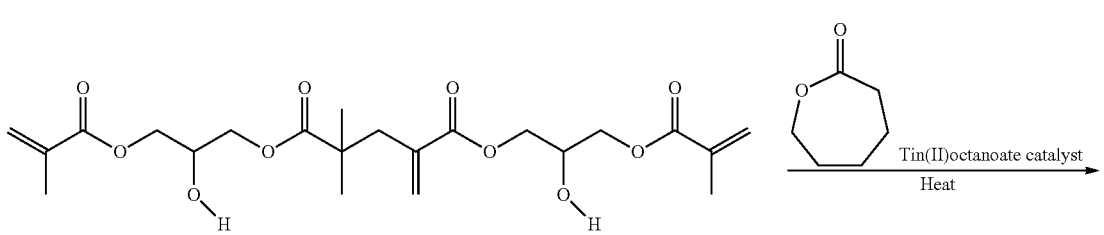

-continued

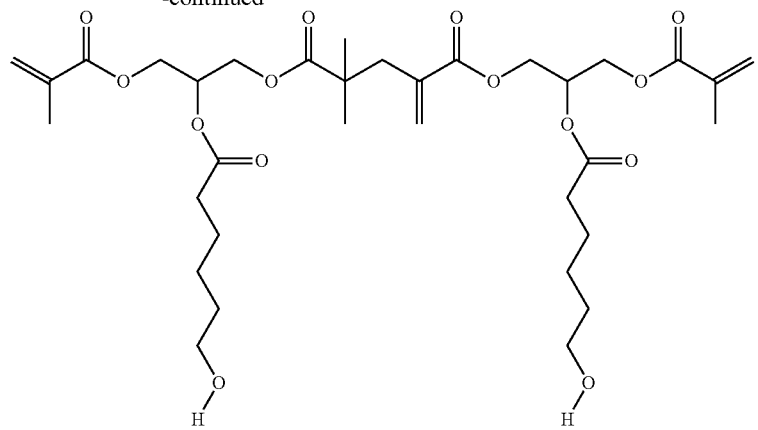

AFM-1 (32 g, 0.07 mol), caprolactone (16 g, 0.14 mol), tin(II)octanoate (0.05 g) and BHT (0.08 g) were charged into a 100 mL round bottom flask equipped with a mechanical stirrer and dry air flowing through the flask to a bubbler and a condenser. With continuous stirring, the mixture was heated at 130-140 C overnight to provide a viscous yellow liquid in 95% yield. NMR confirmed the structure.

Example 16

Preparation of AFM-Caprolactonyl Phosphate

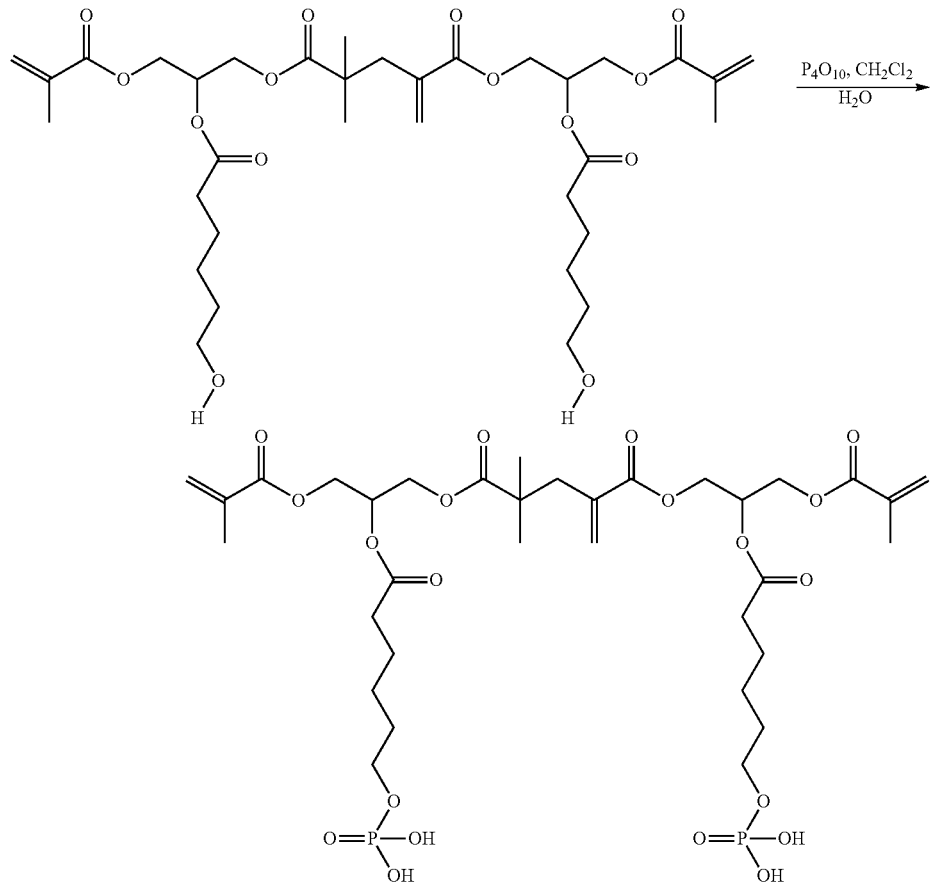

Phosphorous pentoxide ($P_4O_{10}$, 5.10 g, 0.0180 mol) was suspended in 10 mL of $CH_2Cl_2$ in a 500 mL 3-neck round bottom flask. The flask was pre-dried with a heat gun as nitrogen was purged through, then cooled to room temperature under nitrogen. The flask was also equipped with a mechanical stirrer, a temperature controller and nitrogen streaming through the flask into a nearby bubbler and a dropping funnel. A solution of AFM-caprolactone (24.5 g, 0.0358 mol) in 50 mL $CH_2Cl_2$ was added slowly to the suspension in about 30 minutes. The dropping funnel was replaced with a condenser. The mixture was refluxed for 45 minutes. The heat was turned off and, after cooling to room temperature, water (0.68 g, 0.038 mol) was added followed by resumption of refluxing for another 45 minutes. After cooling to room temperature, the mixture was filtered, then concentrated to yellow oil with 90% yield. $^{31}P$ NMR confirmed the presence of P nuclei Example 17

Preparation of AFM-Trimellitic Acid Adduct

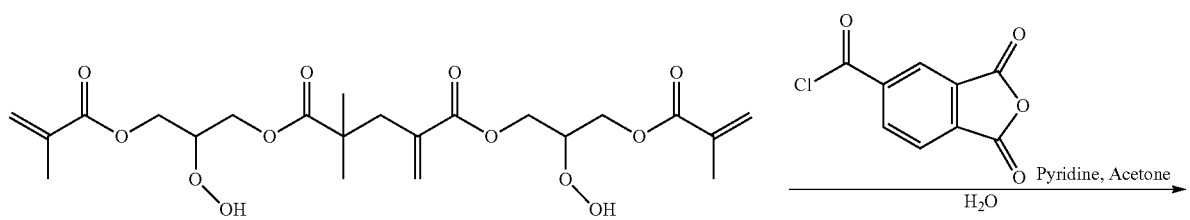

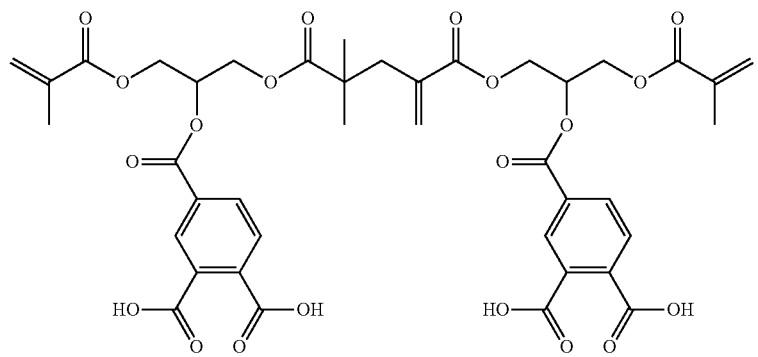

Trimellitic acid anhydride chloride (32.40 g, 0.154 mol) was dissolved 100 mL acetone in a 3-neck flask under nitrogen. The flask was cooled in an ice bath. The solution was stirred continuously while a solution of AFM-1 (35.25 g, 0.0773 mol), and pyridine (12.32 g, 0.154 mol) in 50 ml of acetone was added slowly to the cold solution using a dropping funnel. After addition was completed, the flask contents were continuously stirred at room temperature for 4 hours. Water (2.77 g, 0.154 mol) was added and stirring at room temperature was continued overnight. Then the solid formed was removed by vacuum filtration and washed with acetone. The filtrate was concentrated and dried to a white solid with 73% yield. The structure confirmed by NMR.

Example 18

Preparation of AFM-Caprolaconyl Trimellitic Acid

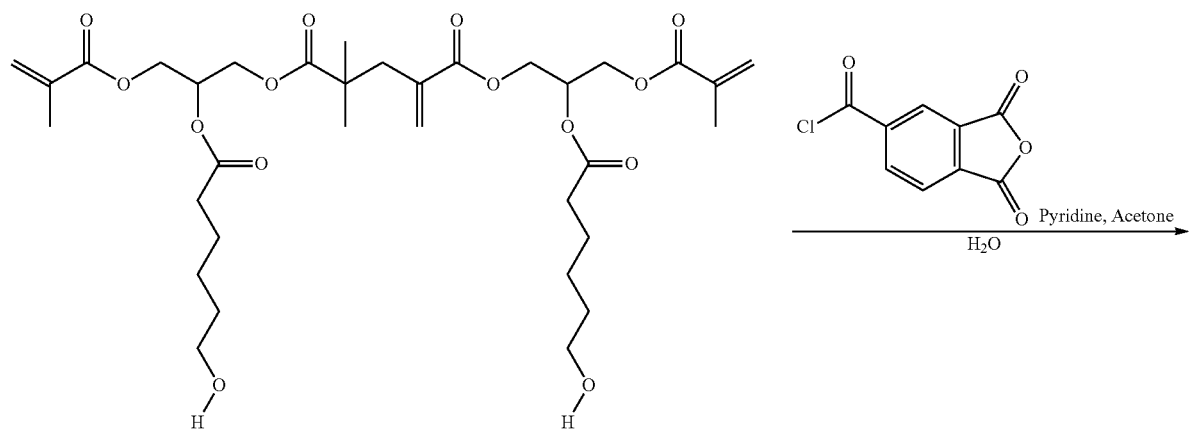

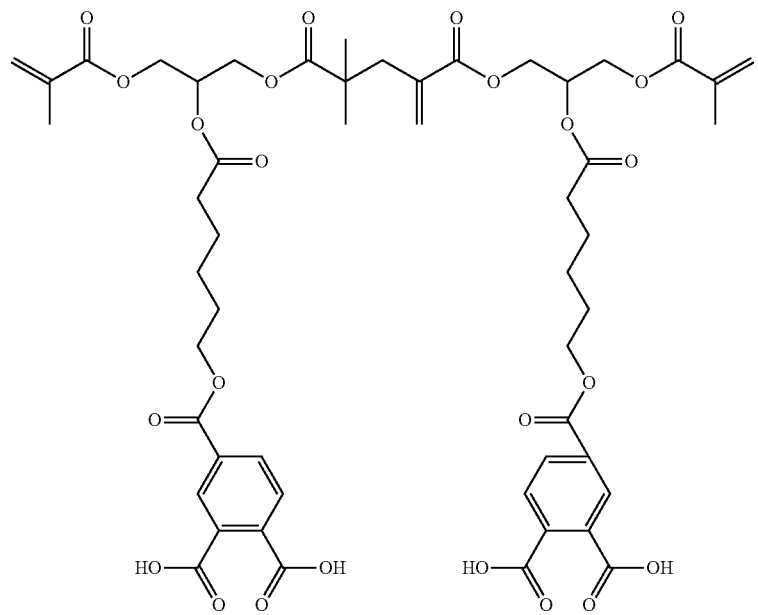

Trimellitic acid anhydride chloride (50 g, 0.240 mol) is dissolved in 150 mL acetone in a 3-neck flask under nitrogen. The flask is cooled in an ice bath. A solution of AFM-caprolactone intermediate (82.05 g, 0.12 mol), and pyridine (19.0 g, 0.240 mol) in 80 ml of acetone is added slowly through a dropping funnel while continuously stirring the cold solution. After addition is completed, the flask contents are continuously stirred at room temperature for 4 hours. Water (4.32 g, 0.240 mol) is added and the solution is stirred continuously at room temperature overnight. The solids formed are removed by vacuum filtration and washed with acetone. The filtrate is concentrated and dried to yield the product Examples 19-24

Control Examples C3-C4—Resin Compositions

Resin compositions were prepared by mixing the AFMs from Examples 2, 3, 4, 16, and 17 with the components shown in Tables 5 and 6 to form uniform mixtures. The components are in amounts by weight percent. Examples 19-22 were prepared and tested with Control Example C3, and Examples 23-24 were prepared and tested with Control Example C4.

The resin compositions were tested for the amount of deflection (Stress) in micrometers (μm) and the depth of cure (DOC) in millimeters (mm) according to the test procedures described above. The test results in Tables 5 and 6 shows that increasing the amount of AFM in the resin composition reduced the amount of deflection of the cusp in the Stress Test during curing of the resin. The Depth of Cure values were acceptable for use as a dental composite.

TABLE 5

| | Resin Compositions - weight % | | | | | | | | |
|---|---|---|---|---|---|---|---|---|---|
| Component | C3 | Example 19 | | Example 20 | | Example 21 | | Example 22 | |
| AFM | None | Ex 3 | | Ex 2 | | Ex 16 | | Ex 17 | |
| AFM | 0.00 | 2.00 | 4.00 | 2.00 | 4.00 | 2.00 | 4.00 | 2.00 | 4.00 |
| BisGMA | 17.2 | 16.34 | 15.48 | 16.34 | 15.48 | 16.34 | 15.48 | 16.34 | 15.48 |
| HEMA | 8.0 | 7.60 | 7.20 | 7.60 | 7.20 | 7.60 | 7.20 | 7.60 | 7.20 |
| UDMA | 4.0 | 3.80 | 3.60 | 3.80 | 3.60 | 3.80 | 3.60 | 3.80 | 3.60 |
| MHP | 10.0 | 9.50 | 9.00 | 9.50 | 9.00 | 9.50 | 9.00 | 9.50 | 9.00 |
| CPQ | 0.16 | 0.152 | 0.144 | 0.152 | 0.144 | 0.152 | 0.144 | 0.152 | 0.144 |
| EDMAB | 0.44 | 0.418 | 0.396 | 0.418 | 0.396 | 0.418 | 0.396 | 0.418 | 0.396 |
| DPIHFP | 0.20 | 0.19 | 0.18 | 0.19 | 0.18 | 0.19 | 0.18 | 0.19 | 0.18 |
| Z250 | 60.00 | 60.00 | 60.00 | 60.00 | 60.00 | 60.00 | 60.00 | 60.00 | 60.00 |
| | | | | Test results | | | | | |
| Deflection - μm | 5.94 | 3.95 | 2.33 | 4.36 | 2.72 | 4.18 | 3.34 | 4.35 | 3.18 |
| DOC - mm | 3.89 | 3.56 | 3.28 | 3.66 | 3.40 | 3.74 | 3.47 | 3.81 | 3.61 |

TABLE 6

| | Resin Compositions - weight % | | | | |
|---|---|---|---|---|---|
| Component | C4 | Example 23 | | Example 24 | |
| AFM | None | Ex 3 | | Ex 4 | |
| AFM | 0.00 | 2.00 | 4.00 | 2.00 | 4.00 |
| BisGMA | 17.40 | 16.53 | 15.66 | 16.53 | 15.66 |
| HEMA | 11.60 | 11.02 | 10.44 | 11.02 | 10.44 |
| MHP | 10.00 | 9.50 | 9.00 | 9.50 | 9.00 |
| CPQ | 0.32 | 0.30 | 0.29 | 0.30 | 0.29 |
| EDMAB | 0.48 | 0.46 | 0.43 | 0.46 | 0.43 |
| DPIHFP | 0.20 | 0.19 | 0.18 | 0.19 | 0.18 |
| Z250 | 60.00 | 60.00 | 60.00 | 60.00 | 60.00 |

TABLE 6-continued

| | Resin Compositions - weight % | | | | |
|---|---|---|---|---|---|
| Component | C4 | Example 23 | | Example 24 | |
| | | Test Results | | | |
| Deflection - μm | 3.62 | 2.57 | 1.74 | 2.86 | 1.91 |
| DOC - mm | 3.58 | 3.13 | 2.89 | 2.90 | 2.63 |

Examples 25-28

Control Example C5—Nanoparticle Fillers with AFM-Silane

Compositions were Prepared Having the Components Shown in Table 7 According to the following procedure. A silica sol (Nalco 2327k) was added to an 8 ounce (235 mL) glass bottle with Teflon-wrapped threads and stirred with a magnetic stir bar. Solutions were prepared by mixing methoxypropanol, Prostab, silane (3-methacryloxy propyl trimethoxysilane), and AFM-silane, prepared as described in Example 8, to a 115 mL amber glass bottle and then added to the silica sol and stirred over approximately 5 minutes.

The glass jar was then sealed with a Teflon-lined metal cap, Teflon tape, and electrical tape. The reaction was heated to 90° C. with stirring. After approximately 18 hours, the reaction mixture was transferred to a 250 mL round-bottomed flask and concentrated to approximately 45 wt % solids in vacuo (approximately half the original volume). Approximately 55 grams of methoxypropanol was added to lower the solids back to approximately 20 wt %. The solution was then concentrated again to approximately 45 wt % functionalized nanoparticle solids (about 50 mL) in vacuo.

Control Example C5 was prepared according to the same procedure except that 100 grams of silica sol (Nalco 2329k sol; 41.33 wt. %) was added to a 16 ounce (470 mL) glass jar with Teflon-wrapped threads. A solution of methoxypropanol (112.5 g), Prostab (0.0250 g of a 0.05 wt. % solution in water) and silane (3.182 g) was added to the silica sol and stirred. No AFM-silane was added.

The wt % solids of each example was determined by adding approximately 0.250 g of the final solution to an aluminum pan and drying in an oven set at 125° C. for 45 minutes. The sample was then removed from the oven, allowed to cool to room temperature, and the mass of the dried sample was measured and used to calculate percent solids in the nanoparticle solution. The functionalized nanoparticle compositions are suitable as fillers in resin compositions.

TABLE 7

| | Nanoparticle compositions - grams | | | | |
|---|---|---|---|---|---|
| Component | Ex 25 | Ex 26 | Ex 27 | Ex 28 | Ex C5 |
| Silica sol - g | 50 | 50 | 50 | 50 | 100 |
| Methoxy propanol - g | 56.25 | 56.25 | 56.25 | 56.25 | 112.5 |
| Silane - g | 2.864 | 2.546 | 1.909 | 1.273 | 3.182 |
| AFM-Silane - g | 0.609 | 1.219 | 2.437 | 3.656 | None |
| Prostab - 0.05 wt % solution in water - g | 0.0125 | 0.0125 | 0.0125 | 0.0125 | 0.250 |
| Final wt % solids | 38.0 | 40.6 | 37.8 | 41.7 | 45.0 |

Example 29

Preparation of 9,9-dimethoxy-4-thioxo-10-oxa-3,5-dithia-9-silaundec-1-yl 2-methylacrylate

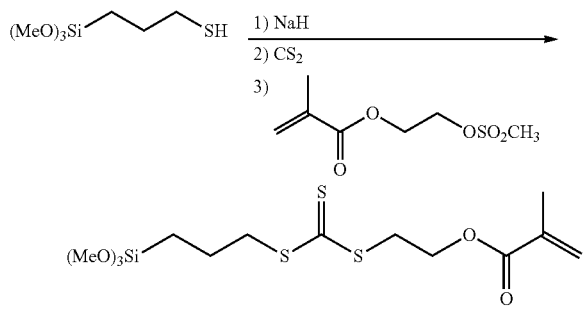

A suspension of sodium hydride in oil 1.15 g, 30 millimole) was washed three times with 10 mL portions of petroleum ether, then tetrahydrofuran (50 mL) was added and the dispersion stirred at room temperature. A solution of (3-mercaptopropyl)trimethoxysilane (5.0 g, 25.5) in tetrahydrofuran (10 mL) was added dropwise. After 30 minutes, a solution of carbon disulfide (2.3 g, 30 millimole, available from EMD Chemicals, Gibbstown, N.J.) in tetrahydrofuran (10 mL) was added dropwise. After one hour, a solution of 2-[(methylsulfonyl)oxy]ethyl 2-methylacrylate (5.3 g, 25.5 millimole) in tetrahydrofuran (10 mL) was added dropwise and the mixture was stirred overnight. Solvent was then removed from the reaction mixture at reduced pressure and the residue taken up in methylene chloride (75 mL) and a saturated solution of sodium chloride in water (50 mL). The layers were separated and the methylene chloride layer was dried over potassium carbonate, filtered, and solvent removed at reduced pressure to leave 6.7 g of the desired product as an orange oil whose structure was confirmed by NMR analyses.

Example 30

Preparation of 3-(triethoxysilyl)propyl 4-vinylbenzyl(trithiocarbonate)

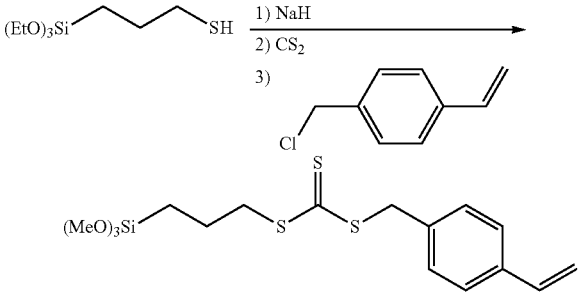

A suspension of sodium hydride in oil (2.3 g, 60 millimole) was washed three times with 15 mL portions of petroleum ether, then tetrahydrofuran (75 mL) was added and the dispersion stirred at room temperature. A solution of (3-mercaptopropyl)triethoxysilane (12.2 g, 51 millimole) in tetrahydrofuran (15 mL) was added dropwise. After 30 minutes, a solution of carbon disulfide (4.6 g, 60 millimole) in tetrahydrofuran (15 mL) was added dropwise. After one hour, a solution of 4-vinylbenzyl chloride (7.8 g, 51 millimole) in tetrahydrofuran (15 mL) was added dropwise and the mixture was stirred overnight. Solvent was then removed from the reaction mixture at reduced pressure and the residue taken up in methylene chloride (150 mL) and a saturated solution of sodium chloride in water (75 mL). The layers were separated and the methylene chloride layer was dried over potassium carbonate, filtered, and solvent removed at reduced pressure to leave 17.8 g of a cloudy orange oil. The orange oil was taken up in petroleum ether (40 mL) and filtered through a 0.2 micron PTFE syringe filter (available from Pall Life Sciences, Port Washington, N.Y.). Solvent was removed at reduced pressure to leave 14.7 g of the desired product as an clear orange oil whose structure was confirmed by NMR analyses.

This disclosure provides the following illustrative embodiments

1. A curable dental composition comprising:
   a) at least one dental resin comprising at least two ethylenically unsaturated group;
   b) an addition-fragmentation agent comprising:
      1) a labile addition-fragmentation group that crosslinks a dental resin polymer;
      2) a free-radically polymerizable group, and
      3) a surface-modifying functional group that associates with the surface of a substrate; and
   c) optionally an inorganic oxide filler.
2. The curable dental resin of embodiment 1 wherein the addition fragmentation agent is of the formula $R^1$-AF-$R^3$, where
   $R^1$ and $R^3$ are each independently $Z_m$-Q-, $Y_p$-Q'-, a (hetero)alkyl group or a (hetero)aryl group with the proviso that at least one of $R^1$ and $R^3$ is $Z_m$-Q-, and with the proviso that at least one of $R^1$ and $R^3$ is $Y_p$-Q'-, Q is a covalent bond or an organic linking group have a valence of m+1; Q' is a covalent bond or an organic linking group have a valence of p+1; Z is an ethylenically unsaturated polymerizable group, m is 1 to 6; p is 1 or 2; and Y is a surface-modifying organic functional group that associates with a substrate on which the addition-fragmentation agent is disposed.

3. The curable dental resin of embodiment 2 wherein the addition-fragmentation group AF is selected from 1,5-diacyl-2,2-dimethyl-4-methylene, dithioesters, trithiocarbamates, trithiocarbonates, thiuram disulfides, xanthates vinyl ethers, allyl sulfides, allyl sulfones, allyl sulfoxides, allyl phosphonates, and allyl peroxides.

4. The dental composition of any of the previous embodiments wherein the addition-fragmentation group 1) is of the formula:

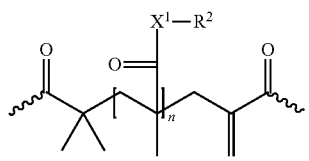

wherein
$R^2$ is $Z_m$-Q-, $Y_p$-Q'-, a (hetero)alkyl group or a (hetero)aryl group
Q is a covalent bond or a linking group, preferably a (hetero)hydrocarbyl linking group, having a valence of m+1;
Q' is a covalent bond or a linking group, preferably a (hetero)hydrocarbyl linking group, having a valence of p+1;
Z is an ethylenically unsaturated polymerizable group, m is 1 to 6;
p is 1 or 2;
Y is an functional group that associates with a substrate on which the addition-fragmentation agent is disposed;
n is 0 or 1.

5. The dental composition of any of the previous embodiments wherein the addition-fragmentation agent is of the formula:

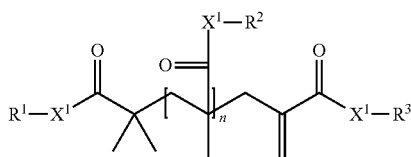

I wherein
$R^1$, $R^2$ and $R^3$ are each independently $Z_m$-Q-, $Y_p$-Q'-, a (hetero)alkyl group or a (hetero)aryl group with the proviso that at least one of $R^1$, $R^2$ and $R^3$ is $Z_m$-Q-, m is 1 to 6;
p is 1 or 2;
and with the proviso that at least one of $R^1$, $R^2$ and $R^3$ is $Y_p$-Q'-
Q is a covalent bond or a linking group, preferably a (hetero)hydrocarbyl linking group, having a valence of m+1;
Q' is a covalent bond or a linking group, preferably a (hetero)hydrocarbyl linking group, having a valence of p+1;
Z is an ethylenically unsaturated polymerizable group,
Y is a functional group that associates with a substrate on which the addition-fragmentation agent is disposed;
m is 1 to 6;
p is 1 or 2;
each $X^1$ is independently —O— or —$NR^4$—, where $R^4$ is H or $C_1$-$C_4$ alkyl, and
n is 0 or 1.

6. The addition-fragmentation agent of any of embodiment 2 to 5 wherein at least one of $R^1$, $R^2$ and $R^3$ contain both $Z_m$-Q- and $Y_p$-Q'-, where
Q is a covalent bond or a linking group, preferably a (hetero)hydrocarbyl linking group, having a valence of m+1;
Q' is a covalent bond or a linking group, preferably a (hetero)hydrocarbyl linking group, having a valence of p+1;
Z is an ethylenically unsaturated polymerizable group, m is 1 to 6;
p is 1 or 2;
and
Y is a functional group that associates with a substrate on which the addition-fragmentation agent is disposed.

7. The dental composition of any of embodiment 2 to 6 wherein Z comprises a vinyl, vinyloxy, (meth)acryloxy, (meth)acrylamido, styrenic and acetylenic functional groups.

8. The dental composition of embodiment 7 wherein Z is selected from:

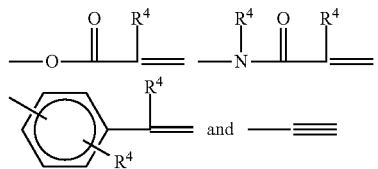

wherein R is H or $C_1$-$C_4$ alkyl

9. The dental composition of any of embodiment 2 to 6 wherein Q is selected from —O—, —S—, —$NR^4$—, —$SO_2$—, —$PO_2$—, —CO—, —OCO—, —$R^6$—, —$NR^4$—CO— $NR^4$—, $NR^4$—CO—O—, $NR^4$—CO—$NR^4$—CO—O—$R^6$—, —CO—$NR^4$—$R^6$—, —$R^6$—CO—O—$R^6$—, —O—$R^6$—, —S—$R^6$—, —$NR^4$—$R^6$—, —$SO_2$—$R^6$—, —$PO_2$—$R^6$—, —CO—$R^6$—, —OCO—$R^6$—, —$NR^4$—CO—$R^6$—, $NR^4$—$R^6$—CO—O—, and $NR^4$—CO—$NR^4$—,
wherein each $R^4$ is hydrogen, a $C_1$ to $C_4$ alkyl group, or aryl group, each $R^6$ is an alkylene group having 1 to 6 carbon atoms, a 5- or 6-membered cycloalkylene group having 5 to 10 carbon atoms, or a divalent arylene group having 6 to 16 carbon atoms, with the proviso that Q-Z does not contain peroxidic linkages.

10. The dental composition of any of embodiment 2 to 6 wherein Q and/or Q' is an alkylene.

11. The dental composition of any of embodiment 2 to 6 wherein Q and/or Q' is an alkylene of the formula —$C_rH_{2r}$—, where r is 1 to 10.

12. The dental composition of any of embodiment 2 to 6 wherein Q and/or Q' is a hydroxyl-substituted alkylene.

13. The dental composition of any of embodiment 2 to 6 wherein Q and/or Q' is —$CH_2$—CH(OH)—$CH_2$—

14. The dental composition of any of embodiment 2 to 6 wherein Q and/or Q' is an aryloxy-substituted alkylene.

15. The dental composition of any of embodiment 2 to 6 wherein Q and/or Q' is an alkoxy-substituted alkylene.

16. The dental composition of any of embodiment 2 to 6 wherein $R^1$—$X^1$— groups, and optionally $R^2$—$X^2$— groups, are selected from $H_2C$=$C(CH_3)C(O)$—O—$CH_2$—CH(OH)—$CH_2$—O—, $H_2C$=$C(CH_3)C(O)$—O—$CH_2$—CH(O—(O)C($CH_3$)=$CH_2$)—$CH_2$—O—, $H_2C$=$C(CH_3)C(O)$—O—CH($CH_2$OPh)—$CH_2$—O—, $H_2C$=$C(CH_3)C(O)$—O—$CH_2CH_2$—N(H)—C(O)—O—CH($CH_2$OPh)—$CH_2$—O—, $H_2C$=$C(CH_3)C(O)$—O—$CH_2$—CH(O—(O)C—N(H)—$CH_2CH_2$—O—(O)C $(CH_3)C=CH_2)-CH_2-O-$, $H_2C=C(H)C(O)-O-(CH_2)_4-O-CH_2-CH(OH)-CH_2-O-$, $H_2C=C(CH_3)C(O)-O-CH_2-CH(O-(O)C-N(H)-CH_2CH_2-O-(O)C(CH_3)C=CH_2)-CH_2-O-$, $CH_3-(CH_2)_7-CH(O-(O)C-N(H)-CH_2CH_2-O-(O)C(CH_3)C=CH_2)-CH_2-O-$, $H_2C=C(H)C(O)-O-(CH_2)_4-O-CH_2-CH(-O-(O)C(H)=CH_2)-CH_2-O-$ and $H_2C=C(H)C(O)-O-CH_2-CH(OH)-CH_2-O-$. $H_2C=C(H)C(O)-O-(CH_2)_4-O-CH_2-CH(-O-(O)C(H)=CH_2)-CH_2-O-$, and $CH_3-(CH_2)_7-CH(O-(O)C-N(H)-CH_2CH_2-O-(O)C(CH_3)C=CH_2)-CH_2-O-$.

17. The dental composition of any of the previous embodiments wherein the ethylenically unsaturated groups of the dental resin are (meth)acrylate groups.

18. The dental composition of any of the previous embodiments wherein the dental resin is an aromatic monomer having a refractive index of at least 1.50.

19. The dental composition of any of the previous embodiments wherein the dental resin is a low volume shrinkage resin.

20. The dental composition of any of the previous embodiments wherein the dental resin is an isocyanurate resin, a tricyclodecane resin, cyclic allylic sulfide resins; methylene dithiepane silane resins; and poly(meth)acryloyl-containing resins, or mixtures thereof.

21. The dental composition of any of the previous embodiments wherein the hardened dental composition exhibits a stress deflection no greater than 2.0, or 1.8, or 1.6, or 1.4, or 1.2, or 1.0, or 0.8, or 0.6.

22. The dental composition of any of the previous embodiments wherein the dental composition further comprises at least one other (meth)acrylate monomer is selected from ethoxylated bisphenol A dimethacrylate, 2-hydroxyethyl methacrylate, bisphenol A diglycidyl dimethacrylate, urethane dimethacrylate, triethlyene glycol dimethacrylate, glycerol dimethacrylate, ethylenegylcol dimethacrylate, neopentylglycol dimethacrylate (NPGDMA), polyethyleneglycol dimethacrylate, and mixtures thereof.

23. The dental composition of any of the previous embodiments wherein the filler inorganic oxide filler comprises nanoparticles.

24. The dental composition of embodiment 23 wherein the inorganic oxide nanoparticles comprise silica, zirconia, or mixtures thereof.

25. The dental composition of embodiments 23-24 wherein the inorganic oxide nanoparticles are in the form of nanoclusters.

26. The dental composition of any of the previous embodiments comprising a surface modified inorganic oxide filler.

27. A method of treating a tooth surface, the method comprising
    a) providing a curable dental resin of any of embodiments 1-26;
    b) placing the dental composition on a tooth surface in the mouth of a subject; and
    c) hardening the hardenable dental composition.

28. The method of embodiment 27 wherein the dental composition is a dental restoration composition.

29. A dental article comprising the curable dental composition of embodiments 1-26 at least partially cured.

30. A method of treating a tooth surface, the method comprising providing an at least partially hardened dental article according to embodiment 29, adhering the dental article on a tooth surface in the mouth of a subject.

31. The dental composition of embodiment 4 or 5 wherein $R^1-X^1-$ groups, and optionally $R^2-X^2-$ groups, are selected from $H_2C=C(CH_3)C(O)-O-CH_2-CH(O-PO_3H_2)-CH_2-O-$, $H_2C=C(CH_3)C(O)-O-CH_2-CH(O-C(O)-(CH_2)_3C(O)OH)-CH_2-O-$, $H_2C=C(CH_3)C(O)-O-CH_2-CH(O-C(O)-(CH_2)_2C(O)OH)-CH_2-O-$, and $H_2C=C(CH_3)C(O)-O-CH_2-CH(O-C(O)-NH-(CH_2)_3Si(OEt)_3)-CH_2-O-$.

32. A universal dental restorative comprising:
    a) 15-30 wt % of a curable dental resin comprising at least two polymerizable, ethylenically unsaturated groups;
    b) 70-85 wt % of an inorganic filler, preferably a surface modified filler,
    c) 0.1 to 10 parts by weight of the addition-fragmentation agent of any of embodiments 1-26, relative to 100 parts by weight of a) and b),
    said curable composition further comprising an initiator and;
    <2%, stabilizers, pigments, etc.

33. A flowable restorative composite comprising:
    a) 25-50 wt % of a curable dental resin comprising at least two polymerizable, ethylenically unsaturated groups;
    b) 50-75 wt % of an inorganic filler;
    c) 0.1 to 10 parts by weight of the addition-fragmentation agent of embodiments 1-26, relative to 100 parts by weight of a) and b).
    d) an initiator,
    e) <2% stabilizers and pigments, and
    f) optionally 5-60 wt. % monomers having a acid-functional group.

34. A resin-modified glass-ionomer adhesive comprising:
    a) 10-25 wt. % of a partially (meth)acrylated poly(meth)acrylic acid;
    b) 5-20% of a hydroxyalkyl (meth)acrylate;
    c) 30-60% of fluoroaluminosilicate (FAS) acid reactive glass);
    d) 0-20% non-acid reactive fillers, preferably surface-treated;
    e) 10-20% water; and
    f) 0.1 to 10 wt. % of the addition-fragmentation agent of embodiments 1-26, relative to 100 parts by weight of a) and b).

35. The resin-modified glass ionomer adhesive of embodiment 34 wherein the floroaluminosilicate is a silane methacrylate surface-treated floroaluminosilicate.

36. A dental adhesive comprising:
    a) 30-8-wt. % mono (meth)acrylate) monomers;
    b) 1-10 wt. % polyfunctional (meth)acrylate monomers;
    c) 5-60 wt. %% monomers having a acid-functional group (including phosphate, phosphonate, carboxylate, sulfonic acids)
    d) 0-10, preferably 1-10 wt. % poly(meth)acrylic acid methacrylate monomers;
    e) 0.1 to 10 wt. % of the addition-fragmentation agent of any of embodiments 1-26, relative to 100 parts by weight of a) to d);
    f) an initiator,
    g) 0-30% inorganic filler, preferably surface modified, relative to 100 parts by weight of a) to d);
    h) 0 to 25 wt. % solvent relative to 100 parts by weight of a) to d);
    i) 0 to 25 wt. % water relative to 100 parts by weight of a) to d); and
    <2% stabilizers and pigments.

37. The curable dental composition of any of embodiments 1-26 further comprising a surface-modified inorganic filler of the formula:

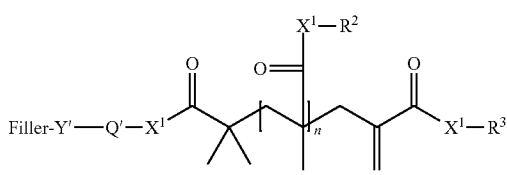

where

Filler is an inorganic filler particle, $R^2$ and $R^3$ are each independently $Z_m$-Q-, $Y_p$-Q'-, a (hetero)alkyl group or a (hetero)aryl group;

Q is a covalent bond or a linking group, preferably an organic (hetero)hydrocarbyl linking group having a valence of m+1;

Q' is a covalent bond or an or a linking group, preferably an organic (hetero)hydrocarbyl linking group having a valence of p+1;

Z is an ethylenically unsaturated polymerizable group,

Y' is the residue of the surface-modifying organic functional group that associates with a substrate on which the addition-fragmentation agent is disposed;

m is 1 to 6;

p is 1 or 2;

$X^1$ is independently —O— or —$NR^4$—, where $R^4$ is H or $C_1$-$C_4$ alkyl, and n is 0 or 1.

38. The curable dental composition of embodiment 37 wherein the Filler is silica.

39. The curable dental composition of any of embodiments 37-38 wherein the group Filler-$Y'_p$— is of the formula Silica-O—Si$(R^7)_2$— wherein each $R^7$ group is independently selected from the group of alkoxy, acetoxy, and halide.

40. The dental composition of embodiment 2 wherein the AF group is a trithiocarbonate group.

What is claimed is:

1. A curable dental composition comprising:
   a) at least one dental resin comprising at least two ethylenically unsaturated groups;
   b) an addition-fragmentation agent of the formula:

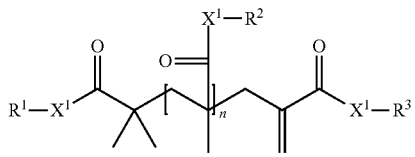

wherein $R^1$, $R^2$ and $R^3$ are each independently $Z_m$-Q-, $Y_p$-Q'-, a (hetero)alkyl group or a (hetero)aryl group with the proviso that at least one of the $R^1$, $R^2$ and $R^3$ is $Z_m$-Q-, and with the proviso that at least one of the $R^1$, $R^2$ and $R^3$ is $Y_p$-Q'-

Q is a covalent bond or a linking group, having a valence of m+1;

Q' is a covalent bond or a linking group, having a valence of p+1;

Z is an ethylenically unsaturated polymerizable group,

Y is a functional group that bonds to, or etches a dental structure on which the addition-fragmentation agent is disposed;

m is 1 to 6;

p is 1 or 2;

each $X^1$ is independently —O— or —$NR^4$—, where $R^4$ is H or $C_1$-$C_4$ alkyl, and n is 0 or 1; and c) optionally an inorganic oxide filler.

2. The dental composition of claim 1 wherein at least on of $R^1$, $R^2$ and $R^3$ of the addition-fragmentation agent contain both $Z_m$-Q- and $Y_p$-Q'-, where Q is a covalent bond or a linking group, having a valence of m+1;

Q' is a covalent bond or a linking group, having a valence of p+1;

Z is an ethylenically unsaturated polymerizable group, m is 1 to 6;

p is 1 or 2; and

Y is a functional group that bonds to, or etches a dental structure on which the addition-fragmentation agent is disposed.

3. The dental composition of claim 2 wherein Z of the addition-fragmentation agent comprises a vinyl, vinyloxy, (meth)acryloxy, (meth)acrylamido, styrenic and acetylenic functional groups.

4. The dental composition of claim 1 wherein Q is selected from —O—, —S—, —$NR^4$—, —$SO_2$—, —$PO_2$—, —CO—, —OCO—, —$R^6$—, —$NR^4$—CO—$NR^4$—, —$NR^4$—CO—O—, —$NR^4$—CO—$NR^4$—CO—O—$R^6$—, —CO—$NR^4$—$R^6$—, —$R^6$—CO—O—$R^6$—, —O—$R^6$—S—$R^6$—, —$NR^4$—$R^6$—, —$SO_2$—$R^6$—, —$PO_2$—$R^6$—, —CO—$R^6$—, —OCO—$R^6$—, —$NR^4$—CO—$R^6$—, —$NR^4$—$R^6$—CO—O—, and —$NR^4$—CO—$NR^4$—, wherein each $R^4$ is hydrogen, a $C_1$ to $C_4$ alkyl group, or aryl group, each $R^6$ is an alkylene group having 1 to 6 carbon atoms, a 5- or 6-membered cycloalkylene group having 5 to 10 carbon atoms, or a divalent arylene group having 6 to 16 carbon atoms, with the proviso that Q-Z does not contain peroxidic linkages.

5. The dental composition of claim 1 wherein Q and/or Q' is an alkylene.

6. The dental composition of claim 1 wherein Q and/or Q' is a hydroxyl-substituted alkylene.

7. The dental composition of claim 1 wherein the ethylenically unsaturated groups of the dental resin are (meth)acrylate groups.

8. The dental composition of claim 1 wherein the dental resin is an isocyanurate resin, a tricyclodecane resin, cyclic allylic sulfide resins; methylene dithiepane silane resins; and poly(meth)acryloyl-containing resins, or mixtures thereof.

9. The dental composition of claim 1 wherein the hardened dental composition exhibits a stress deflection no greater than 0.6.

10. The dental composition of claim 1 wherein the dental composition further comprises at least one other (meth)acrylate monomer is selected from ethoxylated bisphenol A dimethacrylate, 2-hydroxyethyl methacrylate, bisphenol A diglycidyl dimethacrylate, urethane dimethacrylate, triethlyene glycol dimethacrylate, glycerol dimethacrylate, ethylenegylcol dimethacrylate, neopentylglycol dimethacrylate (NPGDMA), polyethyleneglycol dimethacrylate, and mixtures thereof.

11. The dental composition of claim 1 wherein the inorganic oxide filler comprises nanoparticles.

12. The dental composition of claim 1 comprising a surface modified inorganic oxide filler.

13. The curable dental composition of claim 12 comprising a surface-modified inorganic oxide filler of the formula:

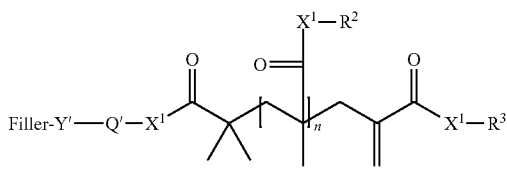

where
Filler is an inorganic oxide filler particle,
$R^2$ and $R^3$ are each independently $Z_m$-Q-, $Y_p$-Q'-, a (hetero)alkyl group or a (hetero)aryl group;
Q is a covalent bond or a linking group, having a valence of m +1;
Q' is a covalent bond or an or a linking group, having a valence of p +1;
Z is an ethylenically unsaturated polymerizable group,
Y' is the residue of the functional group Y;
m is 1 to 6;
p is 1 or 2;
$X^1$ is independently —O- or —$NR^4$—, where $R^4$ is H or $C_1$-$C_4$ alkyl, and
n is 0 or 1.

14. A method of treating a tooth surface, the method comprising
  a) providing a curable dental composition of claim 1;
  b) placing the dental composition on a tooth surface in the mouth of a subject; and
  c) curing the curable dental composition.

15. The curable dental composition of claim 1 comprising a universal dental restorative comprising:
  a) 15-30 wt % of a curable dental resin comprising at least two polymerizable, ethylenically unsaturated groups;
  b) 70-85 wt % of an inorganic filler;
  c) 0.1 to 10 parts by weight of the addition-fragmentation agent of claim 1, relative to 100 parts by weight of a) and b),
  said curable composition further comprising an initiator and;
  <2%, stabilizers, or pigments.

16. The curable dental composition of claim 1 comprising a flowable restorative composite comprising:
  a) 25-50 wt % of a curable dental resin comprising at least two polymerizable, ethylenically unsaturated groups;
  b) 50-75 wt % of an inorganic filler;
  c) 0.1 to 10 parts by weight of the addition-fragmentation agent, relative to 100 parts by weight of a) and b);
  d) an initiator;
  e) <2% stabilizers and pigments, and
  f) optionally 5-60 wt. %% monomers having a acid-functional group.

17. The curable dental composition of claim 1 comprising a resin-modified glass-ionomer adhesive comprising:
  a) 10-25 wt. % of a partially (meth)acrylated poly(meth)acrylic acid;
  b) 5-20% of a hydroxyalkyl (meth)acrylate;
  c) 30-60% of fluoroaluminosilicate (FAS) acid reactive glass;
  d) 0-20% non-acid reactive fillers;
  e) 10-20% water; and
  f) 0.1 to 10 wt. % of the addition-fragmentation agent, relative to 100 parts by weight of a) and b).

18. The curable dental composition of claim 1 comprising a dental adhesive comprising:
  a) 30-8-wt. % mono (meth)acrylate) monomers;
  b) 1-10 wt. % polyfunctional (meth)acrylate monomers;
  c) 5-60 wt. % monomers having a acid- functional group;
  d) 0-10, poly(meth)acrylic acid methacrylate monomers;
  e) 0.1 to 10 wt. % of the addition-fragmentation agent, relative to 100 parts by weight of a) to d);
  f) an initiator,
  g) 0-30% inorganic filler, relative to 100 parts by weight of a) to d);
  h) 0 to 25 wt. % solvent relative to 100 parts by weight of a) to d);
  i) 0 to 25 wt. % water relative to 100 parts by weight of a) to d); and
  <2% stabilizers and pigments.

* * * * *

UNITED STATES PATENT AND TRADEMARK OFFICE
CERTIFICATE OF CORRECTION

PATENT NO. : 9,907,733 B2
APPLICATION NO. : 14/239566
DATED : March 6, 2018
INVENTOR(S) : Guy Joly Page 1 of 2

It is certified that error appears in the above-identified patent and that said Letters Patent is hereby corrected as shown below:

In the Specification

Column 4,
Line 29, delete "2-(2'-phenoxyethoxyl)ethyl," and insert -- 2-(2'-phenoxyethoxy)ethyl, --, therefor.

Column 13,

Lines 1-8, delete " 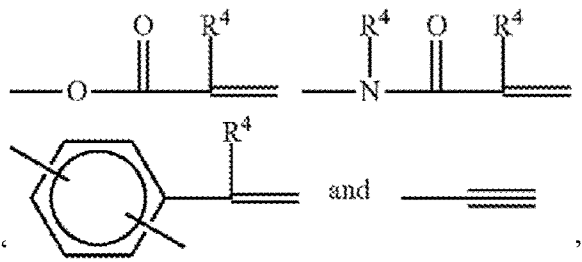 "

and insert -- 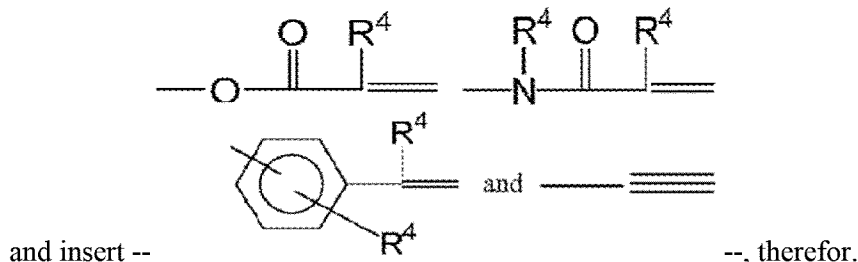 --, therefor.

Column 37,
Line 43, delete "IA" and insert -- 1A --, therefor.

Signed and Sealed this
Ninth Day of October, 2018

Andrei Iancu
*Director of the United States Patent and Trademark Office*

Column 40,
Lines 18-22, delete " 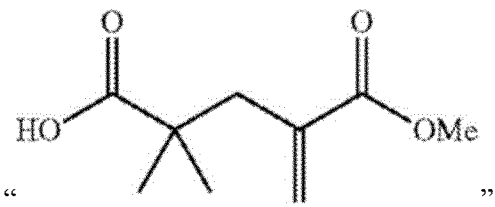 "
and insert -- 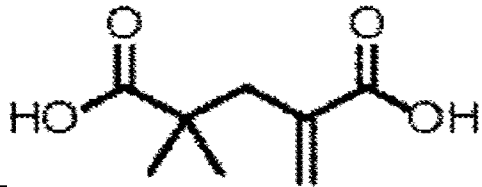 --, therefor.
Column 40,
Lines 25-28, delete " 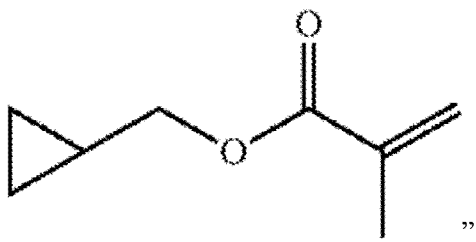 "
and insert -- 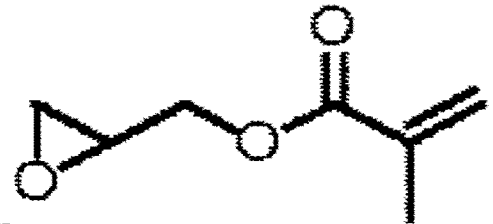 --, therefor.
Column 58,
Line 30, delete "R" and insert -- $R^4$ --, therefor.
In the Claims
Column 61,
Line 57, in Claim 1, delete "the $R^1$," and insert -- $R^1$, --, therefor.